US010078729B2

(12) United States Patent
Ward et al.

(10) Patent No.: US 10,078,729 B2
(45) Date of Patent: Sep. 18, 2018

(54) SYSTEMS AND METHODS FOR CODING DATA FROM A MEDICAL ENCOUNTER

(71) Applicant: T-System, Inc., Dallas, TX (US)

(72) Inventors: James Ward, Plano, TX (US); Richard Wunnebuger, Westcliffe, CO (US); Stephen Hilliard, Richardson, TX (US); Hank Hikspoors, McKinney, TX (US)

(73) Assignee: T-System, Inc., Dallas, TX (US)

( * ) Notice: Subject to any disclaimer, the term of this patent is extended or adjusted under 35 U.S.C. 154(b) by 84 days.

(21) Appl. No.: 14/170,437

(22) Filed: Jan. 31, 2014

(65) Prior Publication Data

US 2015/0220689 A1  Aug. 6, 2015

(51) Int. Cl.
*G06Q 10/00* (2012.01)
*G06Q 50/00* (2012.01)
*G06F 19/00* (2018.01)
*G16H 10/60* (2018.01)

(52) U.S. Cl.
CPC .......... *G06F 19/328* (2013.01); *G06F 19/322* (2013.01); *G06F 19/324* (2013.01); *G16H 10/60* (2018.01)

(58) Field of Classification Search
CPC ........ G06Q 50/22; G06Q 50/24; G16H 10/00; G16H 10/20; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00; G16H 10/40
See application file for complete search history.

(56) References Cited

U.S. PATENT DOCUMENTS

| 8,265,961 B2 | 9/2012 | Callas |
| 8,510,129 B2 | 8/2013 | Morris |
| 2003/0046111 A1* | 3/2003 | Snitkin ............... G06F 19/3481 705/2 |

(Continued)

FOREIGN PATENT DOCUMENTS

WO  WO 2013/116788 A1  8/2013

OTHER PUBLICATIONS

International Search Report and Written Opinion issued for PCT/US2015/013474, dated May 14, 2015, 8 pages.

*Primary Examiner* — Neha Patel
(74) *Attorney, Agent, or Firm* — Norton Rose Fulbright US LLP

(57) ABSTRACT

Systems and methods assist in gathering relevant data in a doctor-patient encounter for obtaining a properly specified diagnosis code. In one embodiment, selectable data items which are provided as part of a medical charting program may be correlated with one or more standardized diagnosis codes (e.g. ICD-10 codes). Upon selection of the appropriate data items when charting a patient encounter, one or more diagnosis codes which are correlated with the selected data items may be flagged and/or generated for later use, such as for filing a claim submission as part of a billing process or to further enhance the clinical workflow of patient encounter documentation.

13 Claims, 39 Drawing Sheets

(56) References Cited

U.S. PATENT DOCUMENTS

| | | | |
|---|---|---|---|
| 2005/0131738 A1* | 6/2005 | Morris | G06F 19/322 |
| | | | 705/2 |
| 2008/0319942 A1* | 12/2008 | Courdy | G06F 19/322 |
| 2010/0094657 A1* | 4/2010 | Stern | G06F 19/322 |
| | | | 705/3 |
| 2010/0305969 A1* | 12/2010 | Bacon | G06F 19/322 |
| | | | 705/3 |
| 2011/0119309 A1 | 5/2011 | Aronson | |
| 2015/0106111 A1* | 4/2015 | Gray | G06F 19/345 |
| | | | 705/2 |

* cited by examiner

T-Site_123

- Home
- Bill Jones 46y
  M  T / □ / ⊕
- Charting
  - History
  - Exam
  - Course
  - Dx / DI
- View
  - Clinical
  - Nurse
  - Feedback
  - Sum of Care
- Print
  - Clinical
  - Instrux/Rx
- Closure
  - Discharge
  - Lock
- Addenda
- Other
  - CPOE
  - Clin Data
  - Vital Signs

[Chart View] [Feedback View]

MORE PHYSICAL EXAM

○ HEAD
  (atraumatic)          scalp tenderness _____ #2 _____
○ HEAD
  (nml inspection)      conjunctival findings _____
  (PERRL)               scleral icterus _____
                        pale conjunctivae _____
○ ENT
  (ears nm)             hemotympanum _____
  (nose nm)             abnml ear exam _____
  (pharynx nm)          nasal injury _____
                        pharyngeal erythema _____
                        tonsillar exudate _____
                        dry mucous membranes _____
○ NECK                  verteb. tenderness _____ painful movmt _____
  (nml inspection)      decrsd ROM _____ muscle spasm _____
  (supple)              carotid bruit _____ JVD _____
  (C sp. non-tendr)     thyromegaly _____
○ CVS                   abnml rate _____ tachycardia _____ bradycardia _____
  (nml rate/rhythm)     abnml rhythm _____ muscle spasm _____
  (heart sounds nml)    murmur _____ JVD _____
  (pulses nml)          extra sounds _____
                        decrsd pulses _____
○ RESPIRATORY           resp distress _____
  (no resp distress)    decreased air movement _____
  (breath sounds nml)   chest wall injury #1 _____ #2 _____
  (chest nontender)     accessory muscles _____
                        rales _____
                        rhonchi _____
                        wheezes _____
○ breast exam _____

○ ABDOMEN               obese _____ scar _____ visible inj _____
  (no visible inj)      tenderness #1 _____ #2 _____
  (soft) / (nontender)  rebound _____ guarding _____
  (fem pulses eql)      abnml bowel snds _____
                        distention _____
  (no mass)             mass _____
  (no organomegaly)     organomegaly _____ gravid uterus _____
  (fem pulses eql)      fem pulse deficit _____
○ FEM GENITALIA         vag bleeding _____ discharge _____
  external exam nml     bimanual tenderness _____
  bimanual exam nml     enlarged uterus _____ mass _____
  speculum exam nml
○ MALE GENITALIA        tenderness _____
  nml genitalia         scrotal swelling _____
  testes descended
○ RECTAL                heme positive _____ color: _____
  nml rectal exam       tenderness _____
  nontender             abnormal digital exam _____
  heme neg stool
○ BACK                  vertebral point tenderness _____
  (nml inspection)      soft tissue tenderness _____
  (nontender)           limited ROM _____
  (ROM nml)
○ SKIN                  cyanosis _____ pallor _____
  (nml color) / (turgo) cool skin _____ diaphoresis _____
  (warm) (dry)          skin rash _____ poor skin turgor _____
  intact
○ NEURO ○ PSYCH         altered mental status _____
  (oriented x3)         CN deficit _____
  (no motor deficit)    weakness _____
  (no sensory deficit)  sensory deficit _____
                        reflex exam: _____
  reflex nml

PROCEDURE NOTES
- ○ Wound Repair ○ Procedural Sedation
- ○ Digital N. Block ○ FRacture Reduction
- ○ Removal Soft Tissue FB ○ Reduction - Dislocated Shoulder
- ○ Removal Soft Tissue FB ○ Reduction - Dislocated Elbow
- ○ Reduction - Nursemaid's Elbow

PROGRESS
TIME -now- _____ stable unstable
vitals: ○ _____ sx's gone much better better unchngd
meds: ○ index ○ mgr _____ exam improved unchanged
[ APPLY ] [ EDIT ] [ DELETE ]

14:29. Patient is stable. Physical exam findings are unchanged.

○ trauma ○ general ○ Resp / CVS ○ CPR ○ re-eval critical care performed by ED physician _____ description
coordination of care _____ ○ DDx ○ MDM ○ scores
D/W Dr. _____ #2 _____ (consult) old records ordered _____
call to Dr. _____ #2 _____ disposition orders written _____
patient/family counseled _____ other: _____
additional history _____

_____ disposition
○ admitted _____ ○ discharged
observation _____ condition: good stable
transferred _____ _____ MSE _____

X-RAYS
nml / NAD  except as noted
independently viewed by me    discussed w/ radiologist _____
interp. by me contemporaneosly    interp. by radiologist _____

R                                                    L skull (-) +        orbits (-) +
facial (-) +       mandible (-) +
nasal (-) +        soft neck (-) +
                   c-spine (-) + clavicle (-) +     Tpsn(-)         clavicle (-) +
scapula (-) +      CXR(-) +        scapula (-) +
shoulder (-) +     sternum(-) +    shoulder (-) +
humerus (-) +      ribs(-) +       humerus (-) +
elbow (-) +        KUB(-) +        elbow (-) +
forearm (-) +      LS(-) +         forearm (-) +
wrist (-) +        sacrum(-) +     wrist (-) +
hand (-) +         pelvis (-) +    hand (-) +
digit (-) +        IVP(-) +        digit (-) + hip (-) +                          hip (-) +
femur (-) +                        femur (-) +
knee (-) +                         knee (-) +
patella (-) +                      patella (-) +
tib/fib (-) +                      tib/fib (-) + ankle (-) +                        ankle (-) +
foot (-) +                         foot (-) +
toe (-) +                          toe (-) +

EKG / LABS / SPECIAL STUDIES
○ EKG nml    ○ CT Head NAD    ○ CT C-Spine NAD
○ Labs nml   ○ CT Chest NAD   ○ CT Abdomen NAD

---

Chart View | Feedback View

T-Site_123
Home
Bill Jones 46y
M
Charting
- History
- Exam
- Course
- Dx / DI
View
- Clinical
- Nurse
- Feedback
- Sum of Care
Print
- Clinical
- Instrux/Rx
Closure
- Discharge
- Lock
- Addenda
Other
- CPOE
- Clin Data
- Vital Signs

FIG. 14

T-Site_123

Bill Jones  46y
M          T

Charting
- Home
- History
- Exam
- Course
- Dx / DI

View
- Clinical
- Nurse
- Feedback
- Sum of Care

Print
- Clinical
- Instrux/Rx

Closure
- Discharge
- Lock

Addenda
Other
- CPOE
- Clin Data
- Vital Signs

Chart View | Feedback View

○ CLINICAL IMPRESSION        ○ vitals        ○ PRESCRIPTIONS   e-Rx: ○ new  ○ manage wt: ____ acute pain _____  fall  MVA  other: ____                    OTC meds                    ○ NSAIDs              ○ antibiotics
                                                               Acetamin... (OTC) ___        Ibuprofen (600 mg) ___  Augmentin ___
skin _____         fracture                                 OTC meds ___                 Lodine ___              Cephalexin ___
  laceration _____   clavicle ___                                                        Naproxen ___            Cipro ___
  abrasion(s) _____  humerus ___                            ○ pain / nausea              ○ muscle relax          Duricef ___
  skin avulsion _____ radius ___                            Lortab ___                   Flexeril ___            Erythromycin ___
  puncture wound _____ ulna ___                               Tylenol w/ Cod ___           Robaxin ___             Levaquin ___
  foreign body, soft tissue  carpal ___                        Vicodin ___                  Skelaxin ___            Silvadene ___
  burn ___ 1st ___ 2nd ___ 3rd ___  metacarpal ___             Zofran ___                   Soma ___
                        phalanx ___
soft tissue / NVT (UE)  dislocation / separation / sublux
  sprain _____       shoulder ___ elbow ___                 ○ DISCHARGE INSTRUCTIONS                          ○ Pepid
  muscle strain _____ wrist ___ digit ___
  contusion _____   AC joint separation ___                  treatment              ○ activity / work-school
  crush injury _____ nursemaid's elbow ___                  ice _____              no restrictions _____
  tendonitis _____  finger tip injury ___                  elevate _____          rest _____
  tendon laceration __  #2 ___  subungual hematoma ___         sling _____            limit use of hand _____
  nerve injury _____ nail avulsion ___                      splint ____ cast ____    no work w hand _____
                        nail bed lac ___                       elastic wrap _____     RT work _____ off work _____
                        tip amputation, finger ___             buddy tape fingers _____ RT school _____ off school _____
                                                               wound care _____       warnings _____
                      general                                  burn dressing _____    complications _____
  abnormal test _____  hypertension ___                      _____ diet ____ infection _____ Tet given _____
  diabetes _____   lifestyle / substance, finger ___     no diet restrictions ___ sedative meds given _____
  _____                                         clear liquids only _____ return if problems _____

_____ more diagnoses _____                               follow-up                               ○ CPT
○ Allergy          ○ Infectious Disease   ○ Orthopedics
○ Cardiology       ○ Int Medicine, Gen'l  ○ Pediatrics         ○ w/ Dr _____ specialist _____ tests _____
○ Dermatology      ○ Mouth/Dental         ○ Psychiatrics       ○ w/ Dr _____                  ○ medication reconciliation
○ ENT  ○ Eye       ○ Pulmonary            ○ Toxicology         your Dr ____ return to: ED UC    follow up contact #: _____
○ Environmental    ○ Neurology            ○ Trauma             understanding of DC instrux      pt / parent / family _____
○ Gastrointestinal ○ OB-GYN / GU          ○ Urology            verbalized by: _____
                                                               patient left prior to DC instrux review

| Chart View | Feedback View |

T-Site_123
Bill Jones  46y
M

Home
Charting
 History
 Exam
 Course
View
 Dx / DI
 Clinical
 Nurse
 Feedback
 Sum of Care
Print
 Clinical
 Instrux/Rx
Closure
 Discharge
 Lock
Addenda
Other
 CPOE
 Clin Data
 Vital Signs ○ CLINICAL IMPRESSION _____ ○ vitals _____  ○ PRESCRIPTIONS   e-Rx: ○ new  ○ manage wt:____
acute pain _____ fall  MVA  other:____                                  OTC meds _____     ○ NSAIDs _____ ○ antibiotics
                                                                            OTC meds  Acetamin... (OTC)__  Ibuprofen (600 mg)__  Augmentin____
    skin                    fracture                                        OTC meds _____ Lodine _____  Cephalexin____
laceration _____        clavicle                                                              Naproxen ___  Cipro____
abrasion(s) Right upper arm humerus    T-humerus                                              □×              ef____
skin avulsion                radius                                                                            romycin____
puncture wound               ulna       (RT)/ LT        HUMERUS FRACTURE                                        uin____
foreign body, soft tissue    carpal                                                                             ene____
burn ___ 1st ___ 2nd ___ 3rd_  metacarpa        proximal   surgical neck
   soft tissue / NVT (UE)    phalanx            greater tuberosity  lesser tuberosity
sprain _____             dislocation        (shaft)  distal                                                         ○ Pepid___
muscle strain                shoulder
contusion                    wrist              supracondylar  intercondylar  transcondylar                           rk-school___
crush injury                 AC joint s         medial epicondyle  lateral epicondyle
tendonitis                   nursemaid
tendon laceration ___ #2 ___ fing               (transverse) oblique  spiral  segmental
nerve injury                 subungua            comminuted:  2 fragments  -3-  -4-  -5-
                             nail avulsi         avulsion  torus  greenstick  intra-articular                          ff work___
                             nail bed la        (closed (open) Type 1) 2 3A 3B 3C                                      off school___
                             tip amputa         (nondisplaced) displaced  angulated: mild  mod  severe                 gs___
          general
abnormal test ____           hypertensio         _____                                           Tet given___
diabetes _____             lifestyle / su     add'l humerus fx                                             ven___
                                                                                                              s___
           more diagnoses                       probable possible doubt rule out
○ Allergy           ○ Infectious Disease        _____
○ Cardiology        ○ Int Medicine, Gen'l       Discharge Instructions for:
○ Dermatology       ○ Mouth/Dental              HUMERUS FX (proximal)
○ ENT  ○ Eye        ○ Pulmonary                 ELBOW FX                                                     ○ CPT____
○ Environmental     ○ Neurology                                                          specianst____       ○ meorcationrreconciliation
○ Gastrointestinal  ○ OB-GYN / GU               primary dx   secondary dx        your Dr____  return to: ED UC  follow up contact #:____
                    ○ systems                   ○ Toxicology                     understanding of DC instrux   pt / parent / family____
                                                ○ Trauma                         verbalized by:____
                                                ○ Urology                        patient left prior to DC instrux review

T-Site_123

Bill Jones 46y
M

- Home
- Charting
- History
- Exam
- Course
- Dx / DI
- View
  - Clinical
  - Nurse
  - Feedback
  - Sum of Care
- Print
  - Clinical
  - Instrux/Rx
- Closure
- Discharge
- Lock
- Addenda
- Other
- CPOE
- Clin Data
- Vital Signs Chart View | Feedback View

○ CLINICAL IMPRESSION   ○ vitals acute pain _____ fall MVA other: _____ skin — fracture
- laceration _____ clavicle _____
- abrasion(s) Right: upper arm (humerus) Rt shaft, transverse
- skin avulsion _____ radius _____
- puncture wound _____ ulna _____
- foreign body, soft tissue _____ carpal _____
- burn ___ 1st___ 2nd___ 3rd _____ metacarpal _____
  phalanx _____ soft tissue / NVT (UE) — dislocation / separation / sublux
- sprain _____ shoulder _____ elbow _____
- muscle strain _____ wrist _____ digit _____
- contusion Right: upper arm _____ AC joint separation _____
- crush injury _____ nursemaid's elbow _____
- tendonitis _____ finger tip injury _____
- tendon laceration ___#2___ subungual hematoma _____
- nerve injury _____ nail avulsion _____
  nail bed lac _____
  tip amputation, finger _____ general
- abnormal test _____ hypertension _____
- diabetes _____ lifestyle / substance, finger _____

— more diagnoses —
- ○ Allergy            ○ Infectious Disease   ○ Orthopedics
- ○ Cardiology         ○ Int Medicine, Gen'l  ○ Pediatrics
- ○ Dermatology        ○ Mouth/Dental         ○ Psychiatrics
- ○ ENT  ○ Eye         ○ Pulmonary            ○ Toxicology
- ○ Environmental      ○ Neurology            ○ Trauma
- ○ Gastrointestinal   ○ OB-GYN / GU          ○ Urology

○ PRESCRIPTIONS   e-Rx: ○ new  ○ manage wt:

| OTC meds | ○ NSAIDs | ○ antibiotics |
|---|---|---|
| OTC meds | Ibuprofen (600 mg) __ | Augmentin ____ |
| Acetamin... (OTC) __ | Lodine ____ | Cephalexin ____ |
| OTC meds | Naproxen ____ | Cipro ____ |
| ○ pain / nausea | ○ muscle relax | Duricef ____ |
| Lortab ____ | Flexeril ____ | Erythromycin ____ |
| Tylenol w/ Cod ____ | Robaxin ____ | Levaquin ____ |
| Vicodin ____ | Skelaxin ____ | Silvadene ____ |
| Zofran ____ | Soma ____ | |

○ DISCHARGE INSTRUCTIONS   ○ Pepid treatment              ○ activity / work-school
- (ice)                    no restrictions
- (elevate)                rest _____
- (sling)                  limit use of hand _____
- splint _____ cast _____ (no work w hand) _____
- elastic wrap _____      RT work _____ off work _____
- buddy tape fingers _____ RT school _____ off school _____
- wound care _____        warnings
- burn dressing _____ diet _____ complications _____
- no diet restrictions _____ infection _____ Tet given _____
- clear liquids only _____ sedative meds given _____
                           (return if problems)

follow-up                                        ○ CPT
- ○ w/ Dr Dr. Johnson in: 2 days as tests _____ ○ medication reconciliation
- ○ w/ Dr _____ specialist _____               follow up contact #: _____
  your Dr _____ return to: ED UC                pt / parent / family _____
  understanding of DC instrux _____
  verbalized by: _____
  patient left prior to DC instrux review

FIG. 26A

T-Site_123

Home
Bill Jones 46y
M
Charting
History
Exam
Course
Dx / DI
View
Clinical
Nurse
Feedback
Sum of Care
Print
Clinical
Instrux/Rx
Closure
Discharge
Lock 12/3/2013-Arm Pain | Longitudinal Reports | Common Reports | Event Log | zTSysPhysician1 | Forms

B I U

Patient: Jones, Bill  Physician Clinical Report
MRN:  Some Hospital Place General
VisitID:  1111 Someplace Rd, Dallas, TX 75244 111-222-3333
46y, M  Registration Date/Time:

*This is a preliminary document and is subject to change

HISTORY OF PRESENT ILLNESS
Chief Complaint: Injury to the right shoulder. The injury happened just prior to arrival. Fell while running and landed on a concrete surface; tripped. Occurred at an athletic field. Patient is experiencing severe pain. Patient denies injury to the head or neck. No other injury.

REVIEW OF SYSTEMS
The patient has had swelling. He has had tingling of the right upper arm. No numbness, suspected foreign ody or skin laceration.

PAST HISTORY
Negative. No history of heart disease, ling disease or GI disease. The patient's domnant hand is the right. He has not had a prior injury to the same area. Tetanus immunization status is up-to-date.
Surgeries: No history of previous surgery.
Additional Surgeries:
no known surgeries.
Medications:
None.
Allergies:
Codeine.

SOCIAL HISTORY:
Light tobacco smoker. No alcohol use or drug use.

ADDITIONAL NOTES
The nursing notes have been reviewed.

(A)

PHYSICAL EXAM
Vital Signs: Blood pressure: 120 / 80. Heart rate: 99. Respiratory rate 18 regular. Temperature: 98.6 oral. Oxygen saturation: 99 % room air.
Appearance: Alert. Oriented X3. No acute distress.
Head: Head atraumatic.
Eyes: Pupils equal, round and reactive to light. Eyes normal inspection.
ENT: Ears normal. Nose normal. Pharynx normal.
Neck: Normal inspection. Neck supple. C-spine non-tender.
CVS: Normal heart rate and rhythm. Heart sounds normal. Pulses normal.
Respiratory: No respiratory distress. Breath sounds normal. Chest nontender.
Abdomen: No visible injury. Soft and nontender. Bowel sounds normal. No organomegaly. No mass. Femoral pulses equal.
Back: Normal inspection. No tenderness. ROM normal.
Skin: Skin warm and dry. Normal skin color. Normal skin turgor.
Extremities: Right arm: severe tenderness, moderate swelling, large abrasion, medium sized ecchymosis and mild deformity consistent with a humerus fracture located in the upper arm. Neurovascular intact distally. No puncture wound or foreign body. Extremities otherwise negative.
Neuro, Vascular and Tendons: Vascular status intact. Sensation intact. Motor intact. Tendon function intact.
Neuro: Oriented X 3. No motor deficit. No sensory deficit.

Abrasion to the right upper arm.
Contusion to the right upper arm.
Closed displaced transverse fracture of the shaft of the right humerus.

INSTRUCTIONS
Apply ice intermittently (15-20 minutes at a time 4-6 times daily). Elevate affected areas above chest level. Wear sling. Do not work with hand.
Warnings: GENERAL WARNINGS: Return or contact your physician immediately if your condition worsens or changes unexpectedly, if not improving as expected, or if other problems arise.
Prescription Medication:
Lortab 5 mg: take 1 to 2 orally every 6 hours as needed for pain. Dispense fifteen (15). No refills. Generic substitute OK.
Follow-up:
Follow up with doctor Dr. Johnson in two days as scheduled. Summary of care provided to patient and family via paper and digital media.

zTSysPhysician1,

Addenda
Other
CPOE
Clin Data
Vital Signs

FIG. 28

T-Site_123

Bill Jones    46y
M
T  □  ⊙
Charting
🏠 Home
📄 History
🔍 Exam
△ Course
◊ Dx / DI
View
☐ Clinical
☐ Nurse
☐ Feedback
☐ Sum of Care
Print
⊕ Clinical
⊕ Instrux/Rx
Closure
📋 Discharge
🔒 Lock
📄 Addenda
Other
↖ CPOE
☐ Clin Data
⊙ Vital Signs

B  I  U | ☰ ☱ ☲ | ≣ ≣ ≣

12/3/2013-Arm Pain | Longitudinal Reports ▼ | Common Reports ▼ | Event Log ▼ | ✓zTSysPhysician1 ▼ | Forms ▼

General Instruction with ExitWriter
Some Hospital Place General
1111 Someplace Rd., Dallas, TX 75244 111-222-3333
Registration Date/Time:

Patient: Jones, Bill
MRN:
VisitID:
46y, M

Thank you for visiting the Some Hospital Place General-Emergency Department.
You have been evaluated today by zTSysPhysician1, for the following condition(s):

Abrasion to the right upper arm.
Contusion to the right upper arm.
Closed displaced transverse fracture of the right humerus. Apply ice intermittently (15-20 minutes at a time 4-6 times daily). Elevate affected areas above chest level. Wear sling. Do not work with hand. GENERAL WARNINGS: Return or contact your physician immediately if your condition worsens or changes unexpectedly, if not improving as expected, or if other problems arise. Lortab 5 mg: take 1 to 2 orally every 6 hours as needed for pain. Dispense fifteen (15). No refills. Generic substitute OK. Follow up with doctor Dr. Johnson in two days as scheduled. Summary of care provided to patient and family via paper and digital media.

INSTRUCTIONS
Apply ice intermittently (15-20 minutes at a time 4-6 times daily). Elevate affected areas above chest level. Wear sling. Do not work with hand.
Warnings: GENERAL WARNINGS: Return or contact your physician immediately if your condition worsens or changes unexpectedly, if not improving as expected, or if other problems arise.
Prescription Medication:
Lortab 5 mg: take 1 to 2 orally every 6 hours as needed for pain. Dispense fifteen (15). No refills. Generic substitute OK.
Follow-up:
Follow up with doctor Dr. Johnson in two days as scheduled. Summary of care provided to patient and family via paper and digital media.

zTSysPhysician1,

CODING SUMMARY
Patient: Jones, Bill          DOS: 12/03/2013          MR#:
Age/sex: 46y/M                Doctor: zTSysPhysician1,  Visit ID:
Template:

--- CASE COMPLEXITY (MARKED ITEMS ONLY) ---
Clinical Impression: Abrasion to the right upper arm. Contusion to the right upper arm. Closed displaced transverse fracture of the shaft of the right humerus.
Symptoms: Chief Complaint: Injury to the right shoulder.
 swelling  tingling
Past History: neg  dominant hand:  tetanus:  none
Tests & Data: independent review ekg/xray  xrays  consultation
Data Score = 3 (Moderate)
Procedures: Course of Care  consultation/records
Disposition:

--- HISTORY AND PHYSICAL SUMMARY (marked items only) ---
H & P Analysis: 4 (does not include medical decision-making considerations).
HPI: 5 elements: Location  Associated Symptoms  Duration  Context  Severity
ROS: 3 elements: Skin  Musculoskeletal  Neurologic
PFSH: 2 elements: Social Hx  Past Hx
Physical Exam Systems: 9 system: Constitutional  Respiratory  Eyes  Skin  Musculoskeletal  Neurologic  ENT  CVS  GI  *Free Text*
Physical Exam Areas: 4 areas: Neck  Head/Face  Abdomen  Back/spine  *Free Text*

--- CPT CODE ASSIGNMENTS ---
Assigned Level  1  2  3  4  5
Procedures: Course of Care  consultation/records
Coder Signature:
This is a partial abstract of information documented in the full record. Codes must use independent judgement in selecting codes.

SYSTEMS AND METHODS FOR CODING DATA FROM A MEDICAL ENCOUNTER

TECHNICAL FIELD

The present application relates to documenting medical encounters and more specifically to coding diagnoses resulting from a doctor-patient encounter.

BACKGROUND

Throughout a doctor-patient encounter a physician generally must keep precise records corresponding to the patient. These patient records include information relating to patient history, current problems, diagnoses for a particular visit, courses of treatment and medical reports. These records serve many functions relating to the actual treatment of the patient in order to safeguard proper care. More recently, proper records and documentation are also required for physicians to create proper billing statements so they can receive payments from a patient's insurance provider for services rendered.

One important aspect that must be provided for in a claims submission to a payment provider is a diagnosis relating to the patient which justifies actions taken by a physician. Without a diagnosis in a claim submission, many actions taken by a physician will not be deemed to be necessary by a payment provider and therefore will not be covered for payment. A diagnosis is usually provided on a claim submission in the form of a code. Currently, codes which are standardized under the International Classification of Diseases 9 standard (ICD-9) are widely utilized. There are approximately 13,000 codes in the ICD-9 standard which cover a broad spectrum of medicine. For billing purposes, a physician will generally employ a biller/coder that takes a physician's written diagnosis and matches it to a specific ICD-9 code and enters it onto a claim form for submission. This system generally works as the codes are sufficiently broad enough that a coder can look up the proper code. Additionally, because a physician may work in specific areas of medicine, a coder can become familiar with common codes.

Beginning on Oct. 1, 2014, many in the medical field will be required to utilize codes in the ICD-10 for billing purposes. ICD-10 utilizes over 68,000 codes and can be very specific (e.g. identifies right versus left side, code allows for description of comorbidities, manifestations, etiology/causation, complications, detailed anatomic location, sequelae, degree of impairment, biologic and chemical agents, phase/stage, lymph node involvement, age related, procedure or implant related, etc.). This raises many issues in the overall practice of medicine both on the billing side and during an actual patient encounter due to the fact that more/different details may be required to determine a proper diagnosis code.

For example, currently if a patient sees a physician because of a broken arm, a physician may note that the patient has a "closed radius shaft fracture" under ICD-9 (which corresponds to code 813.21). However, if the same terminology was utilized under ICD-10, the description would be a "closed unspecified fracture of the shaft of an unspecified radius." Because multiple portions needed to generate a code would remain unspecified, payment to a physician could be delayed or even rejected. Further, it is notable that for the example of a fractured radius there are 27 possible ICD-9 codes whereas there are 2,960 possible ICD-10 codes. Because of this, not only has the billing process been altered by requiring coders to manage more detailed possibilities for diagnoses and procedures, additional data may need to be obtained/documented by a physician during a patient encounter beyond what a physician is accustomed to obtaining during the normal course of practicing medicine.

One current solution to this problem that has been implemented utilizes a natural language processing engine to locate and determine an appropriate code. In this solution, a computing device receives a typed or dictated natural language input and automatically searches the ICD-10 code database for proper diagnosis codes. This solution raises multiple issues. First, the technology underlying the natural language searches is still unreliable and inaccurate. Further, because a physician does not necessarily know what new information is needed, the proper terminology to plug into the natural language algorithm may not be present.

Another approach entails simply conducting a key word search whereupon a physician or billing/coding professional enters a diagnosis and/or other key terms. However, in many cases depending on the type of problems exhibited by a patient, a key word search may yield 500 or more results. These results would then need to be reviewed and a code would be selected. This approach is not always feasible and/or conducive to finding a proper code in an efficient manner. Further, as with the natural language solution, because the physician may not necessarily know what new information is needed, the proper terminology to plug into the search engine may not be present in the patient documentation.

BRIEF SUMMARY

The present application provides for systems and methods which assist in gathering and/or documenting relevant data in a doctor-patient encounter for obtaining a proper, fully specified, diagnosis and/or procedure code. In one embodiment, selectable data items which are provided as part of a medical charting program may be correlated with one or more standardized diagnosis/procedure codes (e.g. ICD-10 codes). Upon selection of the appropriate data items when charting a patient encounter, one or more codes which are correlated with the selected data items may be flagged and/or generated for later use, such as for filing a claim submission as part of a billing process.

In one embodiment, as selectable data items are selected, dynamic tracking of entered information with respect to one or more diagnosis codes may be implemented. For example, as data items corresponding to one or more codes are received, embodiments may track the data items and corresponding codes to determine if one or more data items are needed to definitively select a diagnosis code. When one or more data items are missing, in order to properly code a diagnosis or procedure, embodiments may provide an indication to a user that more information is needed. Embodiments may further display which particular items are needed.

In another embodiment, a diagnosis or procedure code may require a particular selection of data items from different categories. As a data item from such categories are missing, embodiments may provide an indication to the user and may also display which categories of data remain to be addressed in order to properly specify a particular diagnosis code.

In one embodiment, error checking methods may also be implemented such that when a user completes, or finishes a portion of, the data item collection and one or more data entries are missing with respect to a likely diagnosis or procedure, the user may be notified of the deficiencies and provided with information regarding steps that can be completed in order to yield a properly specified code.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding, reference is now made to the following descriptions taken in conjunction with the accompanying drawings, in which:

FIG. 4 illustrates an example display for a medical data entry program in accordance with an embodiment of the present application;

FIG. 5 illustrates an example display for a medical data entry program in accordance with an embodiment of the present application;

FIG. 7 illustrates an example display for a medical data entry program in accordance with an embodiment of the present application;

FIG. 9 illustrates an example display for a medical data entry program in accordance with an embodiment of the present application;

FIG. 12 illustrates an example display for a medical data entry program in accordance with an embodiment of the present application;

FIG. 13 illustrates an example display for a medical data entry program in accordance with an embodiment of the present application;

FIG. 14 illustrates an example display for a medical data entry program in accordance with an embodiment of the present application;

FIG. 15 illustrates an example display for a medical data entry program in accordance with an embodiment of the present application;

FIG. 16 illustrates an example display for a medical data entry program in accordance with an embodiment of the present application;

FIG. 17 illustrates an example display for a medical data entry program in accordance with an embodiment of the present application;

FIG. 18 illustrates an example display for a medical data entry program in accordance with an embodiment of the present application;

FIG. 19 illustrates an example display for a medical data entry program in accordance with an embodiment of the present application;

FIG. 20 illustrates an example display for a medical data entry program in accordance with an embodiment of the present application;

FIG. 21 illustrates an example display for a medical data entry program in accordance with an embodiment of the present application;

FIG. 22 illustrates an example display for a medical data entry program in accordance with an embodiment of the present application;

FIG. 23 illustrates an example display for a medical data entry program in accordance with an embodiment of the present application;

FIG. 24 illustrates an example display for a medical data entry program in accordance with an embodiment of the present application;

FIG. 25 illustrates an example display for a medical data entry program in accordance with an embodiment of the present application;

FIGS. 26A and 26B illustrate an example display for a medical data entry program in accordance with an embodiment of the present application;

FIGS. 27A and 27B illustrate an example display for a medical data entry program in accordance with an embodiment of the present application;

FIG. 28 illustrates an example display for a medical data entry program in accordance with an embodiment of the present application;

FIG. 29 illustrates an example display for a medical data entry program in accordance with an embodiment of the present application;

FIG. 30 illustrates an example display for a medical data entry program in accordance with an embodiment of the present application;

FIG. 31 illustrates an example display for a medical data entry program in accordance with an embodiment of the present application;

FIG. 32 illustrates an example display for a medical data entry program in accordance with an embodiment of the present application;

FIG. 33 illustrates an example display for a medical data entry program in accordance with an embodiment of the present application;

FIG. 34 illustrates an example display for a medical data entry program in accordance with an embodiment of the present application;

FIG. 35 illustrates an example display for a medical data entry program in accordance with an embodiment of the present application;

DETAILED DESCRIPTION

In order to clearly describe the inventive concepts of the present application, the following figures illustrate various screen shots of a common workflow that may be undertaken during a doctor-patient encounter. The illustrated example is implemented in a prototype version of the EV™ program by T-System Incorporated. It is appreciated that the specific medical problems shown, and the order of entry of data items, is provided for the sake of example. The context of the following discussion will illustrate that various methods may be utilized to implement embodiments of the present application.

Figure 1:
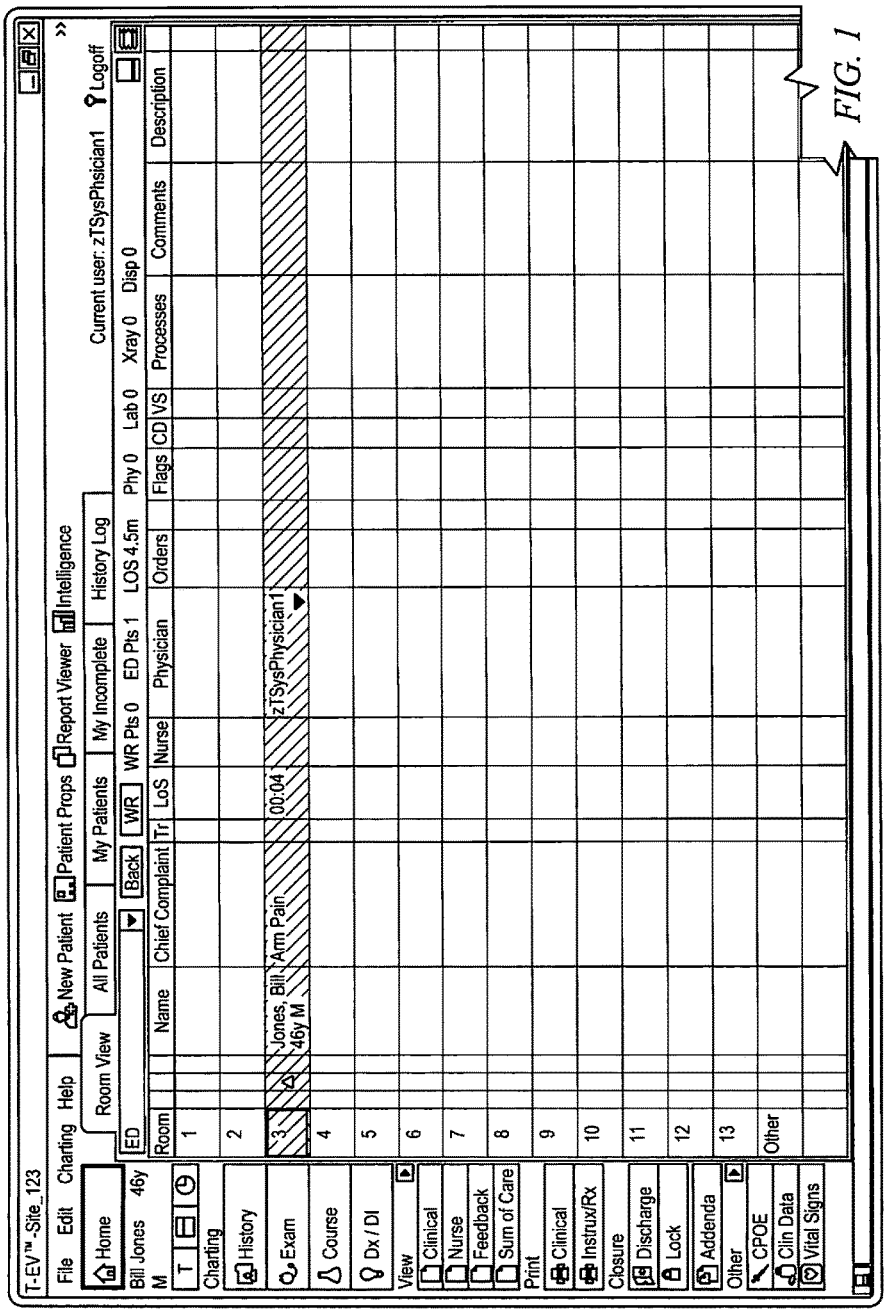
FIG. 1 illustrates an example display for a medical data entry program in accordance with an embodiment of the present application.

FIG. 1 illustrates an initial home screen for a medical data entry program in accordance with an embodiment of the present application. A listing of patients may be provided whereupon a doctor selects a patient that will be or has been encountered. A patient encounter will generally have four portions or categories of information to document. For example, a "History," "Exam," "Course" and "DX/DI" tab on the left side of the screen may be selected which contains a display of selectable data elements for the respective portions of the encounter. The history screen allows data regarding the medical history of the patient and present illness to be entered. The exam screen allows for the entering of data elements representing findings of a physical exam and other tests. The course screen allows for the entry of a course of treatment, results from tests and other information. Finally, the DX/DI screen allows for the entry of data elements pertaining to clinical impressions, diagnoses, discharge instructions and prescriptions.

In many cases, diagnosis or procedure information and a large portion of the data to be received for the purposes of generating a diagnosis/procedure code will be provided by a user under the DX/DI screen. However, embodiments may utilize information from other screens either as contextual information for determining a code, or for actual data entry points. Further, data entered in one or more sections may be imported into other sections for use. For example, a code may require a selection of which arm has been broken (right or left). This information may be entered in the history screen or under the DX/DI screen. When entered in the history screen, such information may be cross-populated where needed.

It is appreciated that the completion and use of the illustrated medical data entry program may be implemented during multiple stages of the encounter (e.g. before, during and/or after). A user may utilize any computing device with sufficient processing resources to implement the described system, e.g. a hand-held tablet device, notebook computer, workstation, etc. Such a device may be connected to a central network (such as one or more of a WAN, LAN, Internet, and the like) and may send/receive data over the network when needed. For example, upon receiving a data entry, a hand-held device may query a remote database for information, receive information and/or store data remotely.

Figure 2:
FIG. 2 illustrates an example display for a medical data entry program in accordance with an embodiment of the present application.

Upon selecting a patient, in this case "Bill Jones," a physician may be presented with a template selection screen shown in FIG. 2. The template selection screen allows a physician (or other medical professional) to select a chief medical complaint. Upon selection of a chief medical complaint, a template of selectable data elements is loaded into the system and data elements pertaining to the selected complaint will be presented in the respective history, exam, course and DX/DI screens. In the illustrated example, the "upper extremity injury" chief medical complaint is selected.

Figure 3:
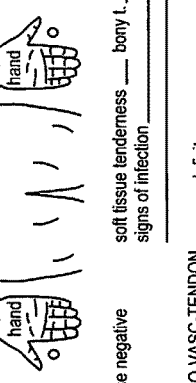
FIG. 3 illustrates an example display for a medical data entry program in accordance with an embodiment of the present application.

FIG. 3 illustrates a history screen in accordance with an embodiment of the present invention. The displayed history screen corresponds to the selected upper extremity injury template. Multiple selectable data elements are provided to a physician/medical professional for selection. One or more of the selectable elements are directed toward the selected chief medical complaint. For example, the upper extremity injury template has selectable data regarding where the injury occurred, e.g. right/left hand, wrist, forearm, elbow, shoulder or clavicle. Other portions may gather additional detail regarding how the injury occurred, when/where it occurred, etc. It is noted that on this particular trauma template physical exam information may also be entered on the history screen as the most relevant information may fit onto a single page (which is usually preferred by the user).

Figure 4:
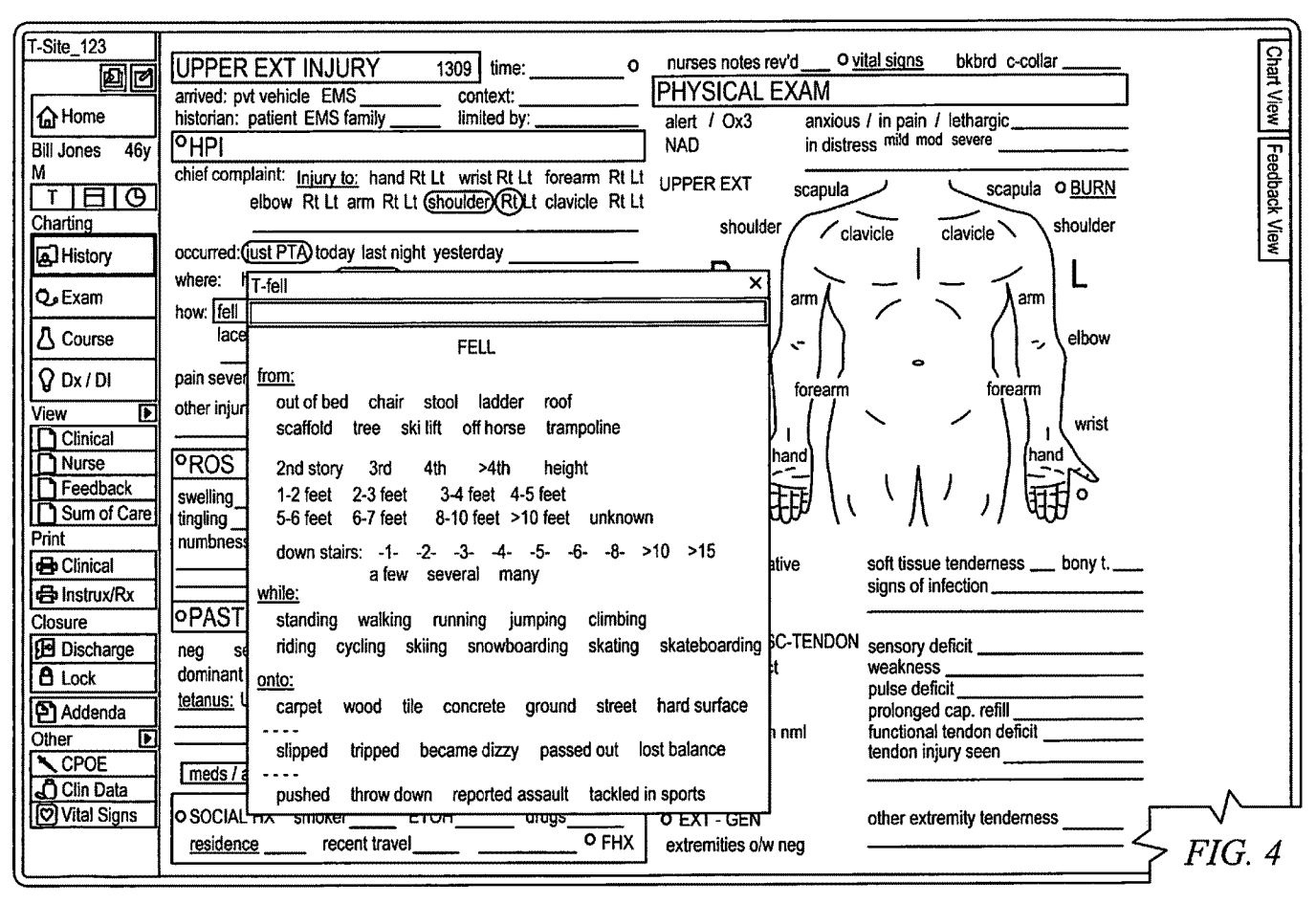
Figure 5:
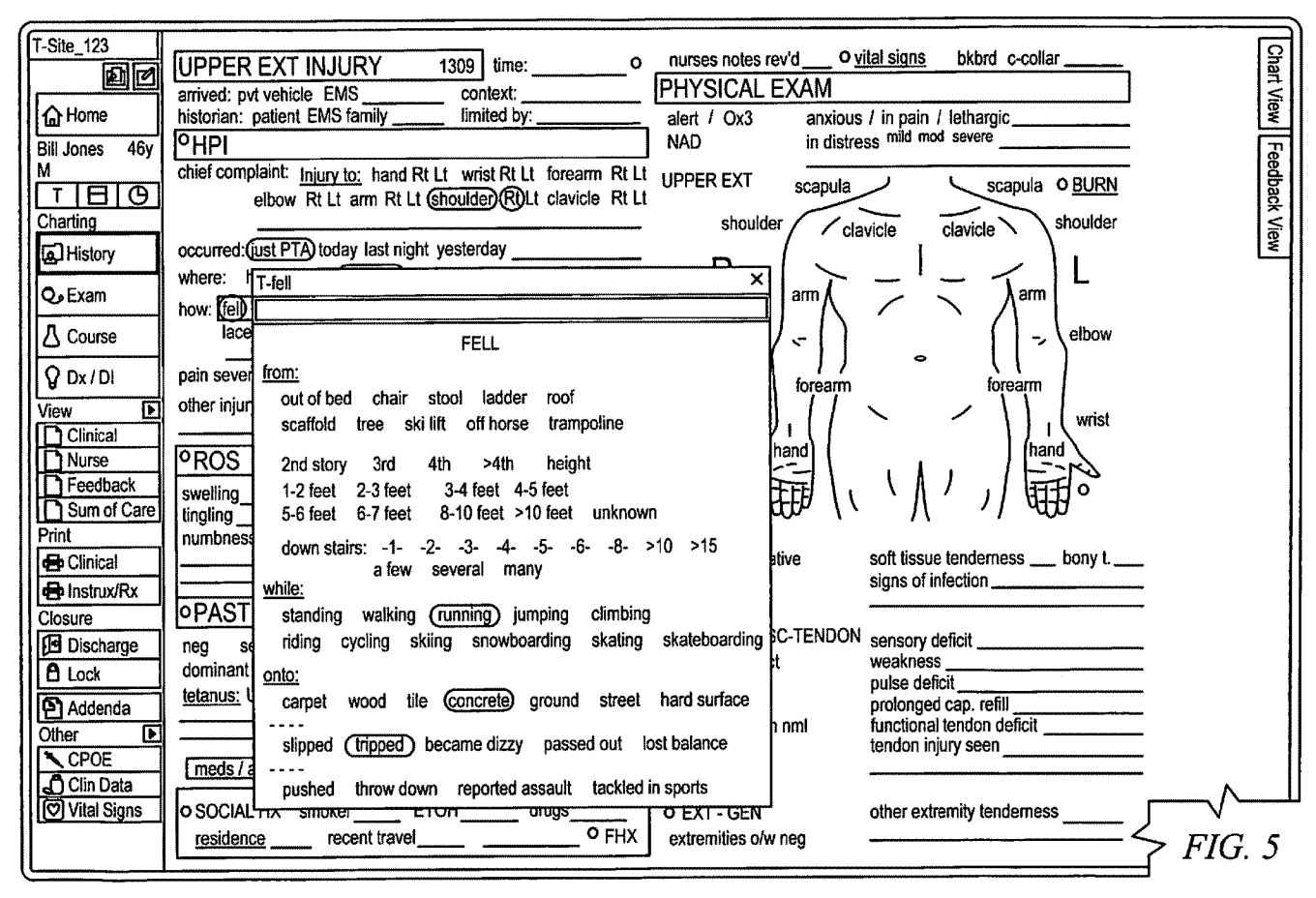

FIG. 4 illustrates the history screen of FIG. 3 having selections of data elements. For example, the medical professional has indicated that the relevant injury is to the right shoulder and it occurred just prior to the patient's arrival at the emergency room. Typically, the medical professional would start marking circles and backslashes to positively select, or to rule out a particular data element, using a right and left mouse click. In the illustrated example the data element corresponding to "fell" is selected and a pop-up screen opens which allows for additional data to be entered. For example, information regarding a fall such as the activity being undertaken, the distance of the fall, etc., may be entered. As can be seen in FIG. 5, the user has selected that the fall occurred while running and onto concrete.

It is appreciated that the collected (or selected) data elements which are entered outside of the diagnosis section may provide information that is correlated to a specific code, such as an ICD-10 CM or PCS code. For example, some ICD-10 codes require a description of the mechanism of action for an injury (W01.198A). This information may be utilized to derive/locate a diagnosis code and/or may be provided to other portions of the medical data entry system where needed to provide information for obtaining a diagnosis code. Further, data points that may not be directly on point to terminology of a diagnosis/procedure code may be utilized to provide context when correlating the selected data to a code. For example, data regarding the height of a fall and the location of landing may provide contextual information regarding the severity of a fall. This information may be utilized to fill in or provide context to allow for the data entry system to suggest possible codes for selection (or to suggest additional data points needed to meet the elements of a particular code).

Figure 6:
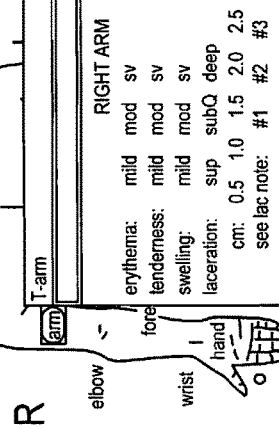
FIG. 6 illustrates an example display for a medical data entry program in accordance with an embodiment of the present application.

Referring now to FIG. 6, the user is now documenting data points from a physical examination of the patient. The user has clicked the entry for the right arm and has received a pop-up allowing for more information to be entered.

It is appreciated that as discussed above, the selection of "right arm" may be imported from other portions (such as a selection in the history portion). Likewise, if right arm was not selected in the history portion, the selection of data elements in the exam portion may backfill entries in the history. Further, any of such entries may be provided forward to the diagnosis/clinical impression sections and a medical professional may review such selections to determine whether they should remain selected for diagnosis purposes. For example, in codes regarding a broken arm, it is now required to specify whether the right or left arm has been injured. The selections discussed herein provide such information for coding. These data points, once entered in one portion, may be carried to other portions of the entry system such as other documentation sections, discrepancy checking sections and the like.

Figure 7:
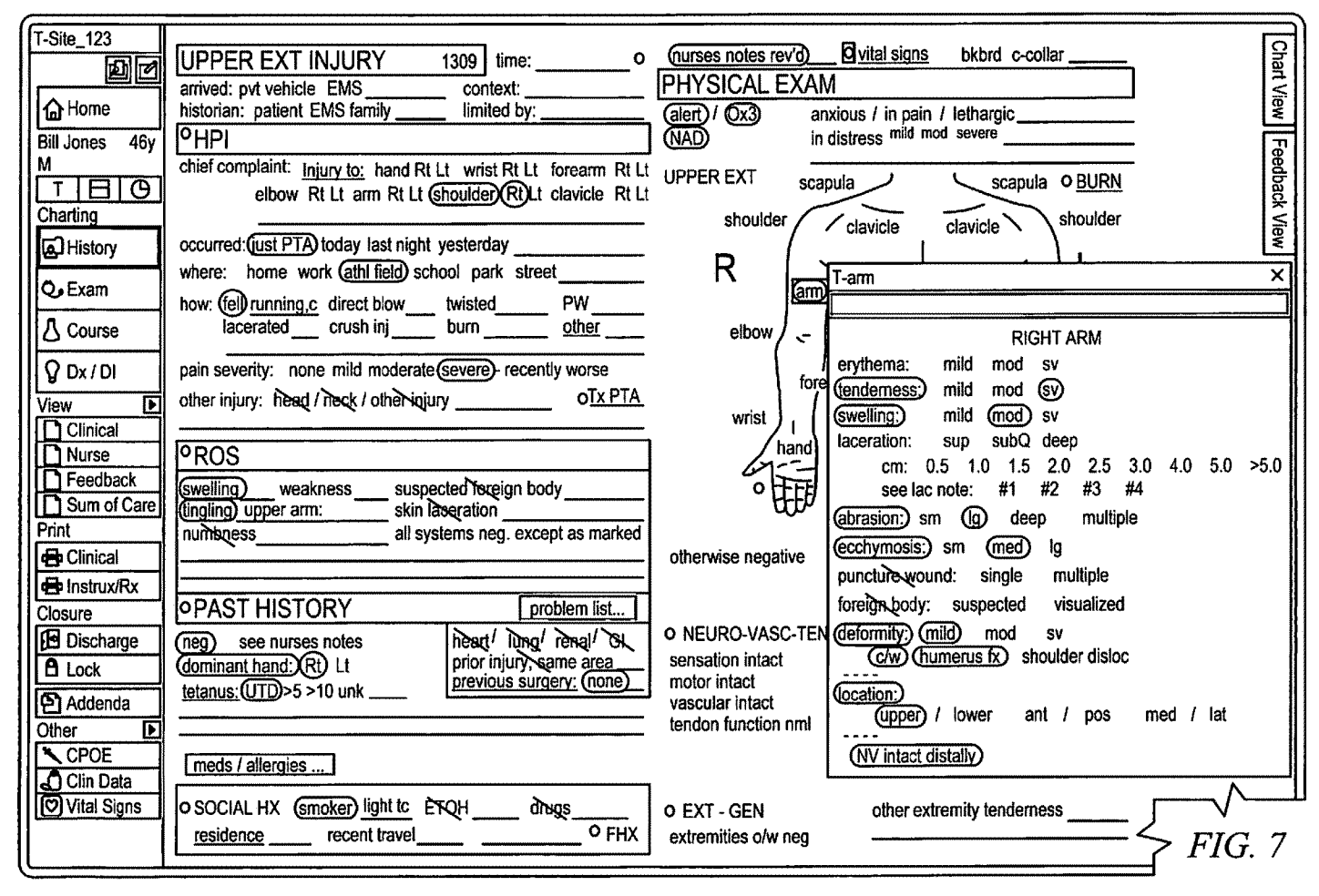

In FIG. 7 various selections in the right arm pop up shown on FIG. 6 are entered. The circles represent positive findings whereas the slashes represent negative findings. It is appreciated that a coder (or an automated program finding a code(s) which is most closely correlated with the entered information) could utilize the findings in the physical examination section even if full findings are not provided by a physician in a diagnosis. For example, the selection of "large abrasion" on the right upper arm could be associated with an ICD-10 code: S40.811A. Likewise, the ecchymosis (contusion) data point could be associated with: S40.021A.

Figure 8:
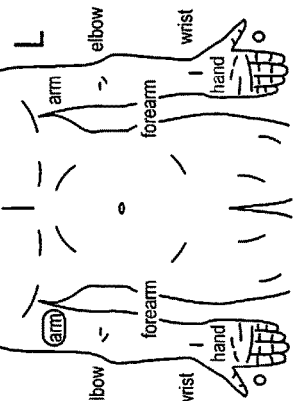
FIG. 8 illustrates an example display for a medical data entry program in accordance with an embodiment of the present application.

FIG. 8 illustrates the documentation of the history tab in completed form for the selected patient. At this point, a user may select the exam tab on the left side of the screen and display the exam template screen at FIG. 9 for the selected upper extremity injury medical complaint. In this case, additional physical examination details may be provided beyond what was provided on the first screen. For example in a fall/trauma example, while the right arm has been indicated as being broken, physical examination of the head, neck, respiratory system, etc., may also be warranted. This portion may function as described above with respect to the history screen. As such, entries on this screen may provide data points or context points to other portions of the system. Further, additional pop up screens may be provided to capture further detail regarding the patient as described above.

Figure 10:
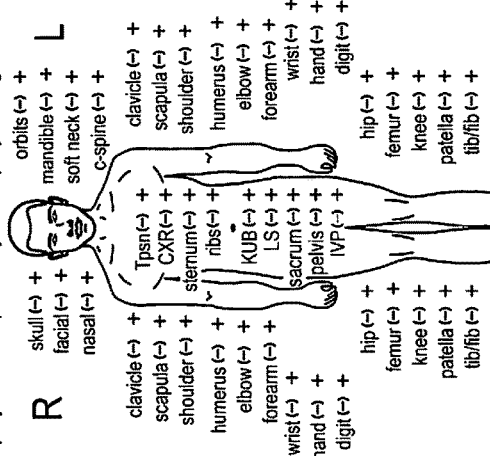
FIG. 10 illustrates an example display for a medical data entry program in accordance with an embodiment of the present application.
Figure 11:
FIG. 11 illustrates an example display for a medical data entry program in accordance with an embodiment of the present application.
Figure 12:
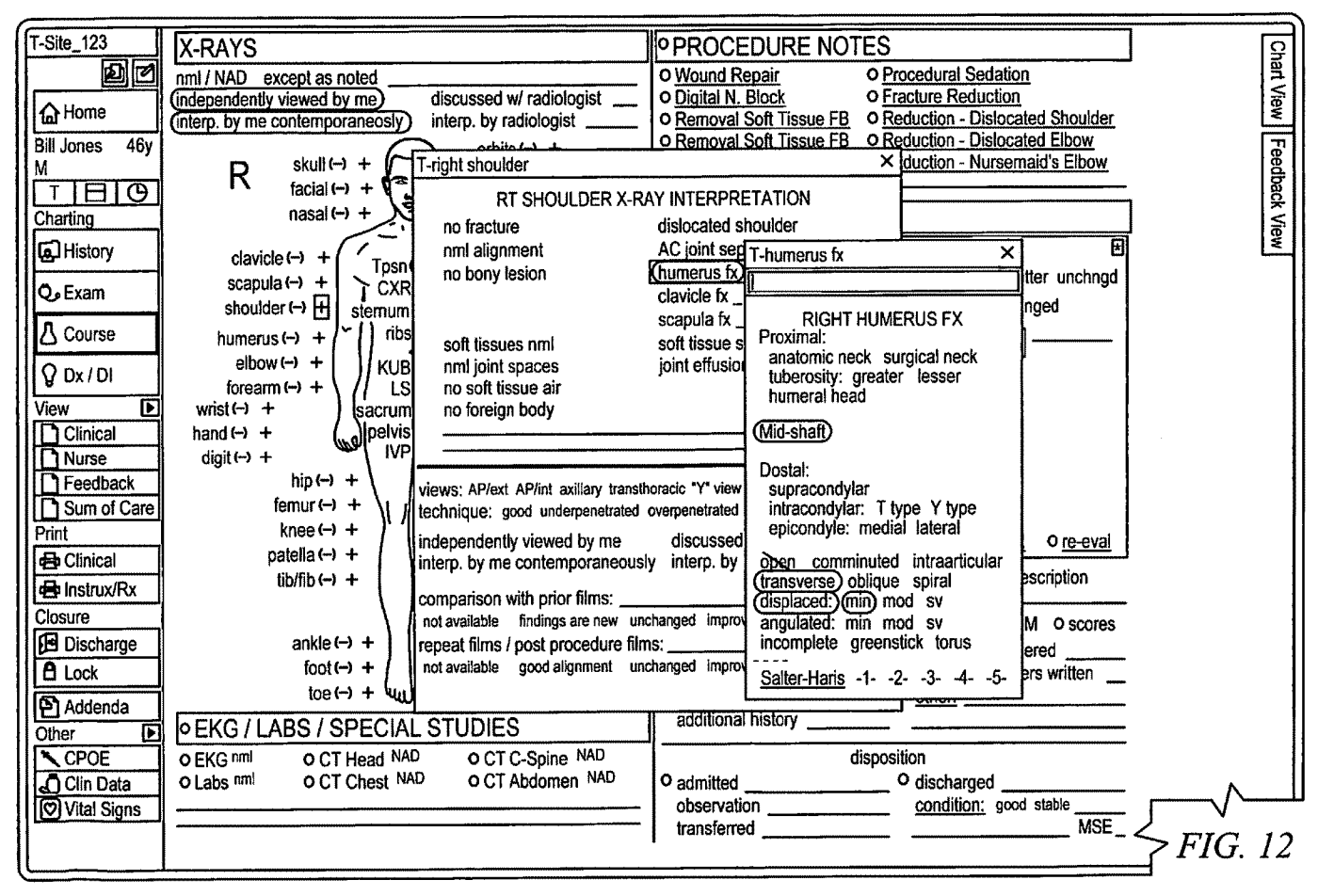

FIG. 10 illustrates the course template screen for the selected upper extremity injury medical complaint of FIG. 2. This page of the template may allow for the user to document test findings, such as for x-ray imaging results along with other notes regarding medical procedures for the patient. Referring to FIG. 11, when the user clicks the "+" sign next to "right humerus," a pop-up for the X-ray interpretation is opened and the user may click on the "humerus fracture" to make a selection. Additional detail may be entered for this selection (shown in FIG. 12) which further describes the fracture such as where the fracture is located, whether the fracture is open, and the like. It is appreciated that the humerus fracture entry and further entries represent further degrees of detail than illustrated in the previous two template screens which merely noted that a broken arm was present. As additional degrees of detail are obtained/documented, each detail may be provided to the diagnosis section for purposes of obtaining sufficient diagnosis code detail to obtain an accurate diagnosis code. A finalized course template form is illustrated at FIG. 13.

Figure 15:
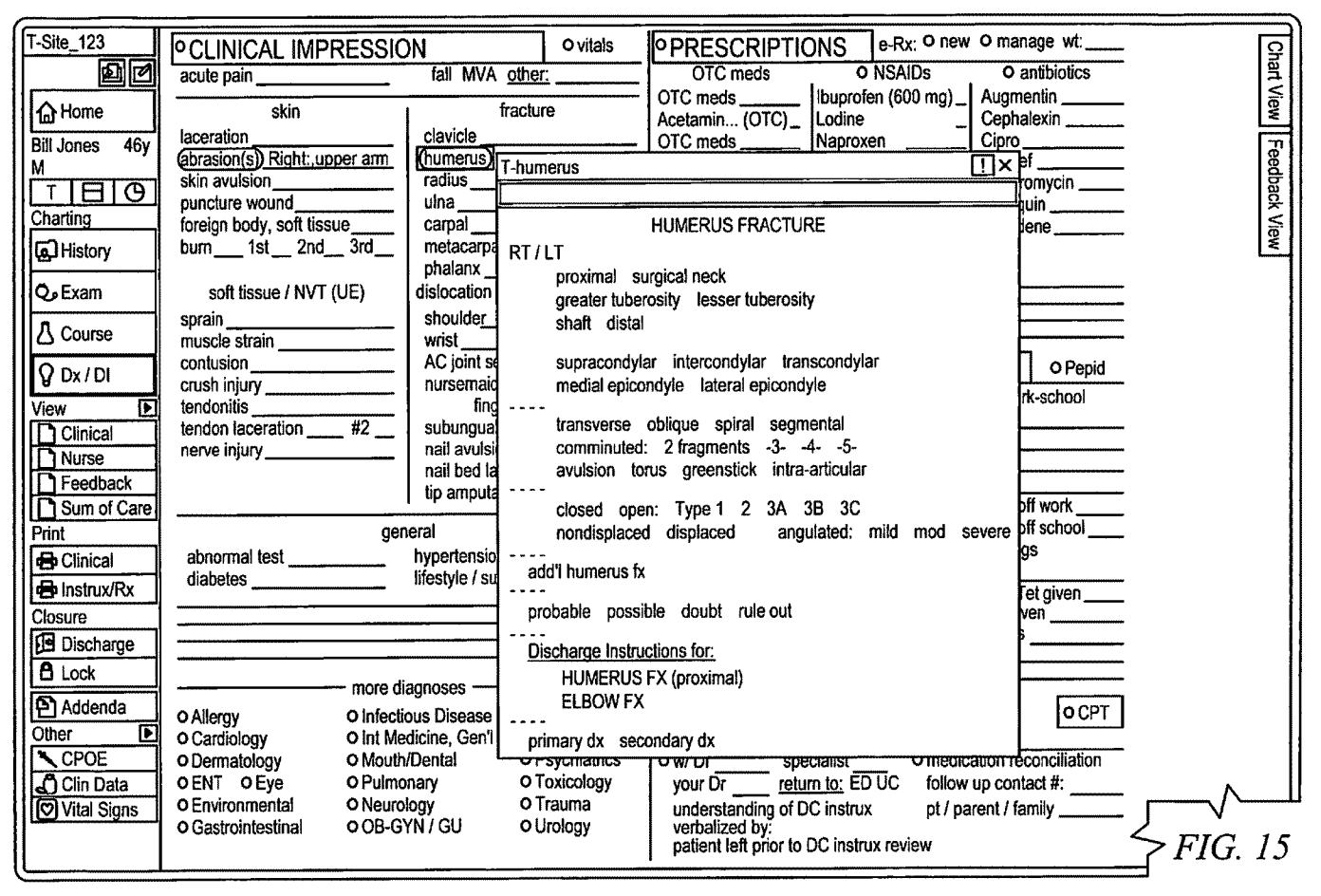

FIG. 14 illustrates the DX/DI template screen for the selected upper extremity injury medical complaint of FIG. 2. On this screen, a user may enter clinical impressions or diagnoses as well as document prescriptions and discharge instructions. In some embodiments, a large portion of the data provided in order to properly classify a diagnosis/procedure code may be entered and obtained/documented at this template screen. Referring to FIG. 15, the physician has entered information regarding clinical impressions. For example, an abrasion on the right upper arm is noted. Additionally, a humerus fracture has also been selected and a pop up window having additional data elements pertaining to the humerus fracture is provided. As stated above, information regarding a humerus fracture may already be imported into the diagnosis screen. In another embodiment, indications that such information may be present may also be provided so as to notify the physician that specific information exists while still allowing the physician to enter the diagnosis himself or herself. Such a notification may be provided as a listing, a different form of selection (e.g. highlights over data items, greyed boxes, checkboxes and the like). It is appreciated that in some clinical scenarios medical professionals may select the DX/DI template screen and provide this information before documenting the history, exam, and test results as described previously. The order of such entries are not fixed in a particular manner. Further, as information from a history/exam entry portions may be forward populated, likewise DX/DI entries may be backward populated.

Figure 16:
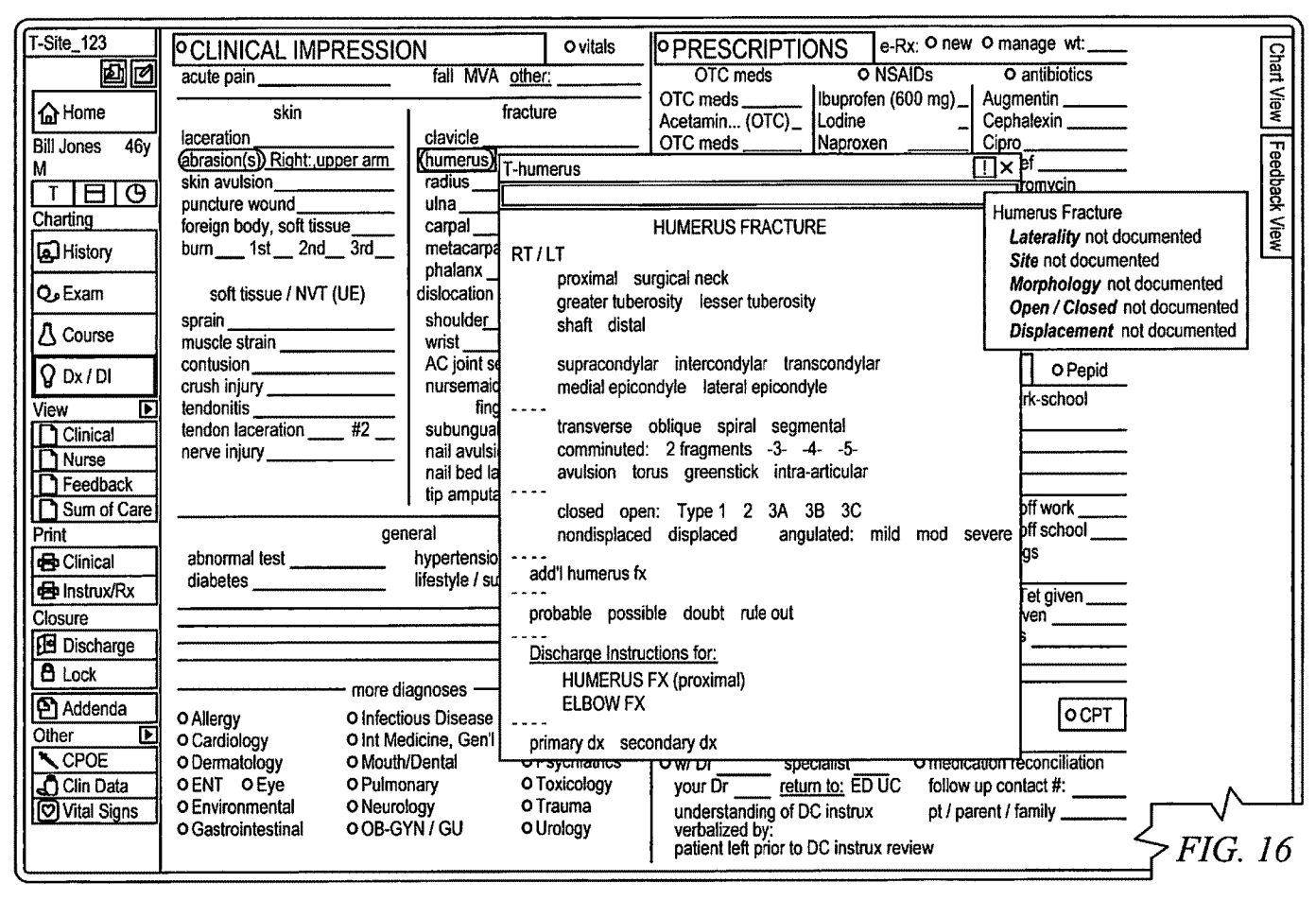

Upon selection of humerus fracture, the pop up window provides detailed data items for selection. In the illustrated embodiment of FIG. 15, the pop-up window also includes an indication in the top right corner (in this case, an exclamation point) that connotes that insufficient information exists to select a fully specified diagnosis code. Upon clicking or hovering (or any other input indication) over the exclamation point as shown on FIG. 16, missing items pertaining to one or more diagnosis codes are listed. Such items may be individual items or may represent categories of items in which one or more data items should be selected. For example, the missing items include a selection as to whether the fracture is open or closed, whether the fracture is located on the right or left arm (laterality), etc. A physician will likely readily know the answer to these data elements, but would not necessarily have previously known that an answer was needed in order to provide adequate findings for obtaining a properly specified diagnosis code. Accordingly, embodiments may obtain data as part of a patient encounter. This data may be correlated with possible diagnosis codes to determine whether one or more codes could be selected. Once the possible codes are known, the system may prompt the physician to enter more information in order to refine the obtained/documented data and to further match a possible diagnosis code.

Figure 17:
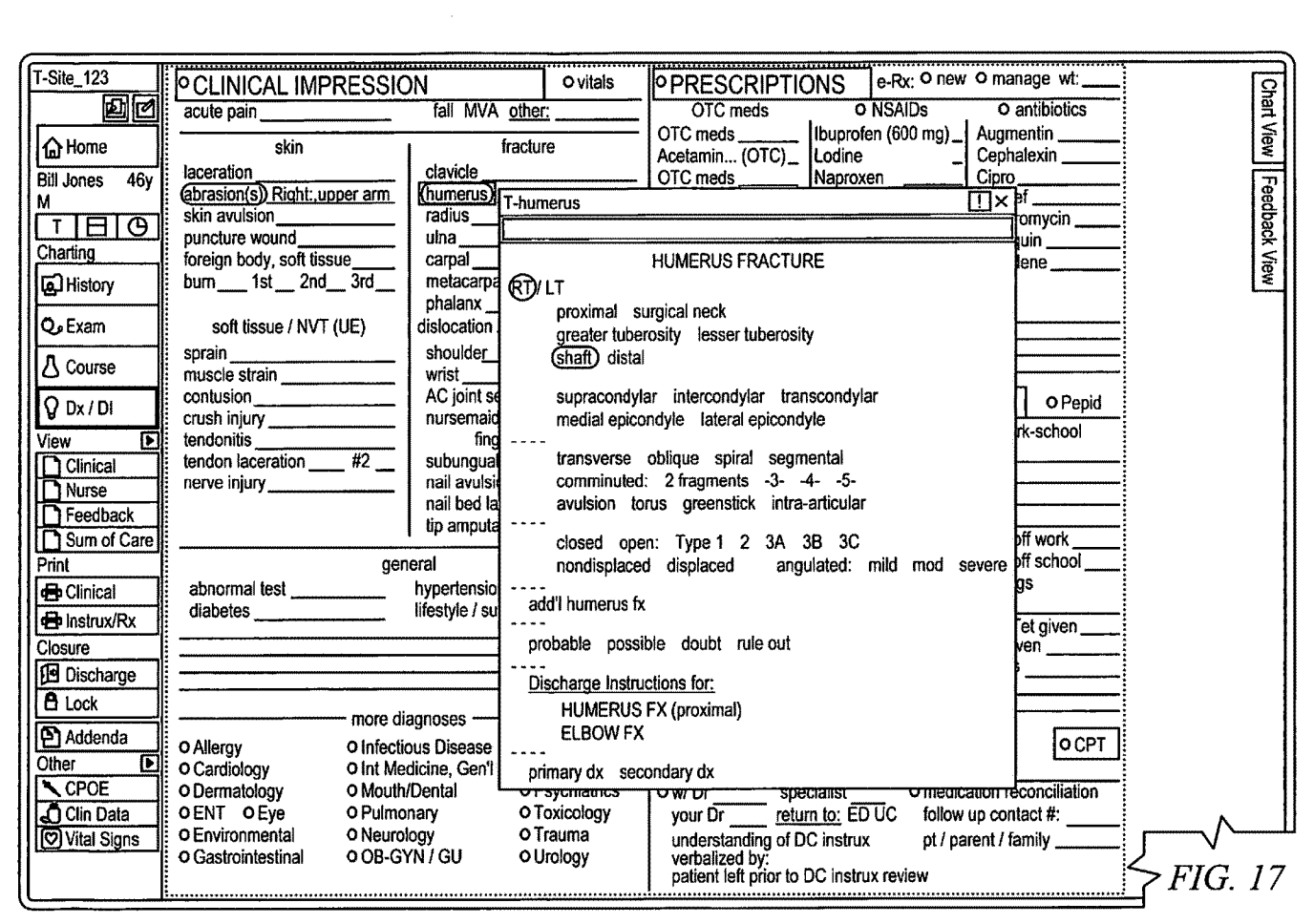
Figure 18:
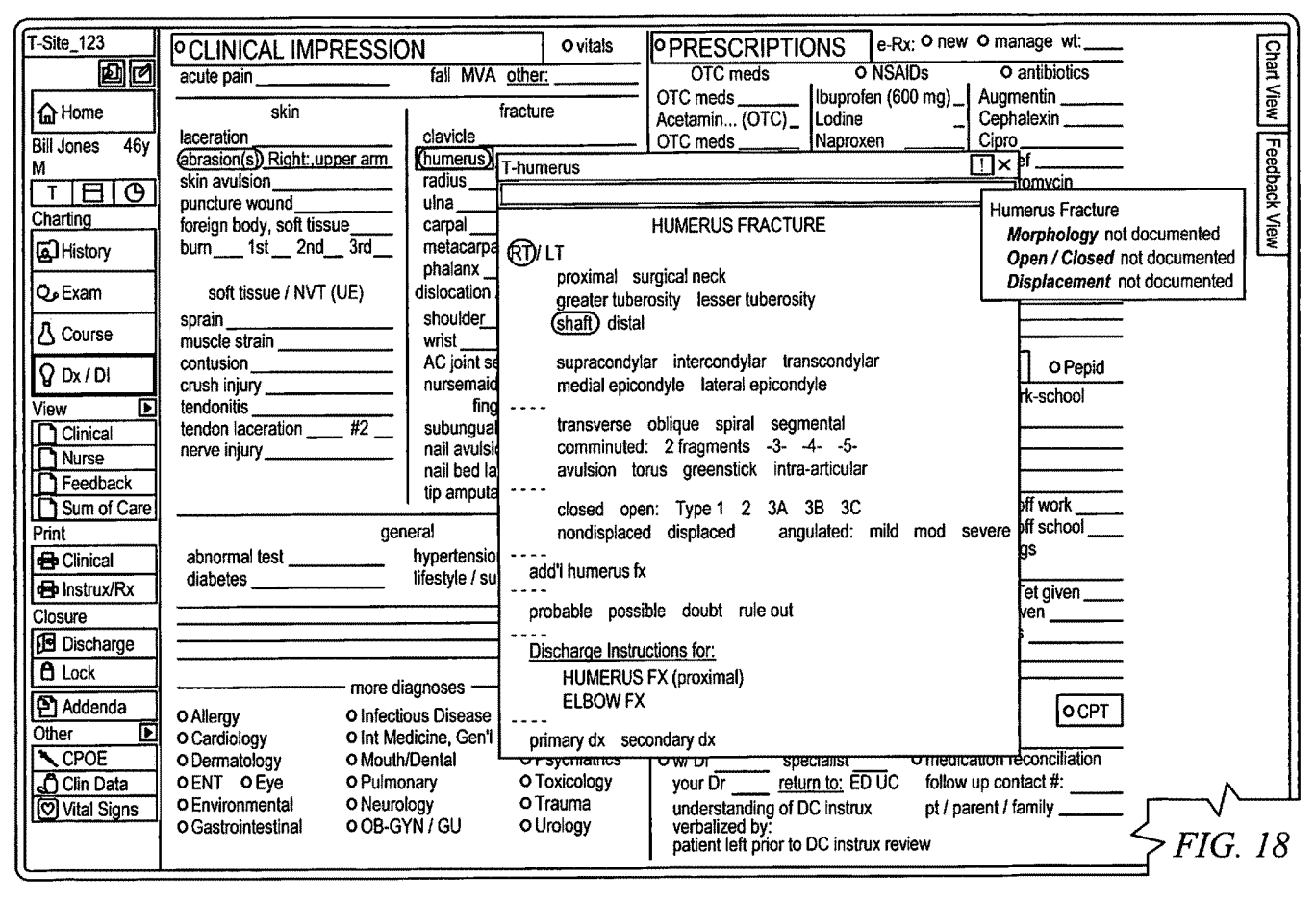
Figure 19:
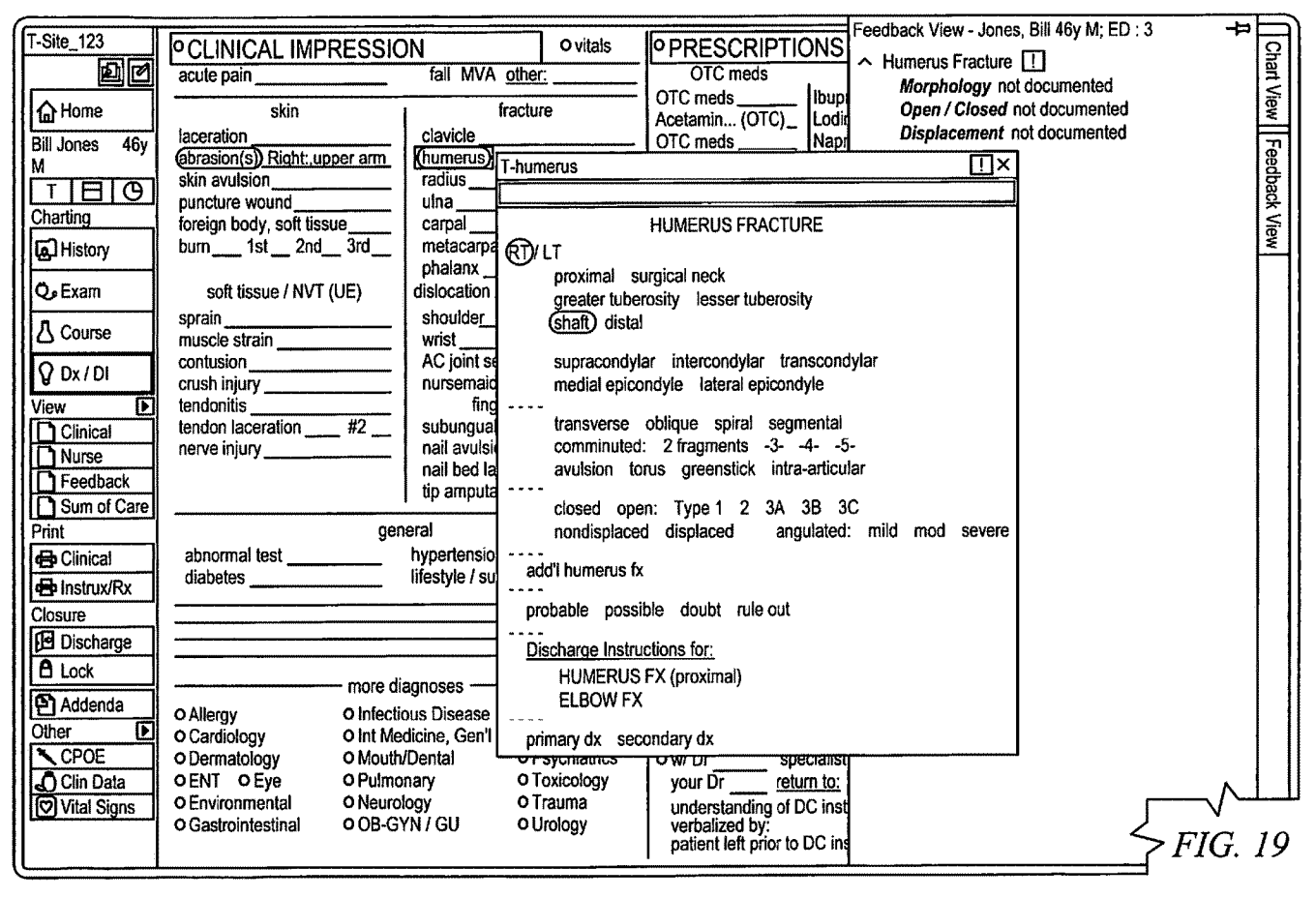
Figure 20:
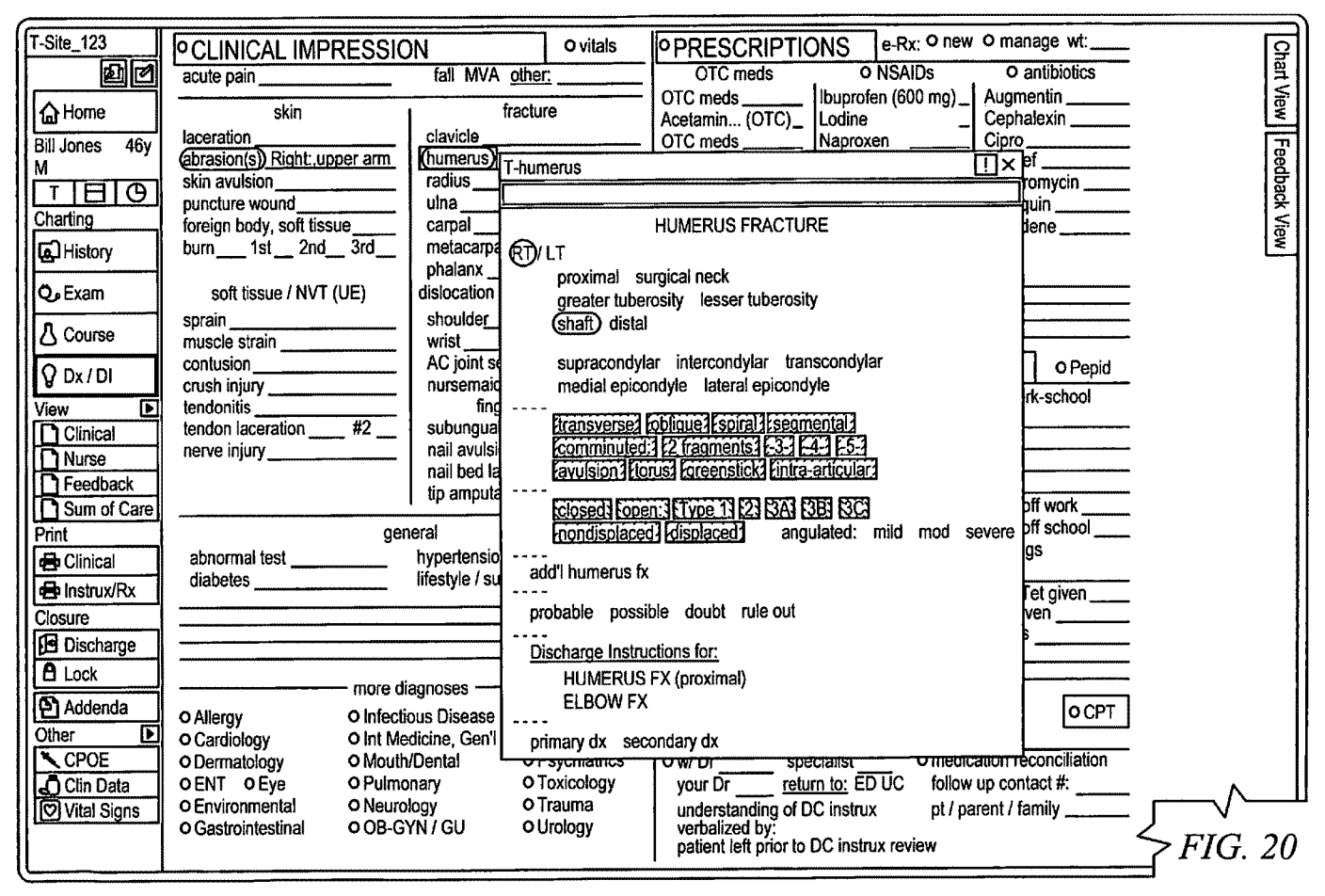

At FIG. 17, the user has selected that the fracture is on the right side of the patient and that site of the fracture is on the shaft portion of the bone. Accordingly, at FIG. 18 when the user clicks/hovers/etc. on the exclamation point, two of the previous entry categories are removed because appropriate data for matching a diagnosis code has been obtained. FIG. 19 illustrates an alternate embodiment where a separate frame may be utilized to track possible errors or deficient data. Such a frame may be provided outside of the detail pop up screens and may document where a user needs to enter additional data for clinical or coding purposes. In some aspects, the data in the side frame may be linked to particular areas in the entry system in order to allow a user to jump to an area to provide additional detail FIG. 20 illustrates another embodiment where deficiencies in received information are indicated to a user. In this example, a user may still click the exclamation point in the upper corner of the humerus fracture pop up window. However, as shown previously, the missing information may correspond to one or more categories of information of which at least one data item should be selected. Such categories may be highlighted in different colors or any other indication which distinguishes categories may be provided. In the illustrated example, in order to complete a correlated diagnosis code, the user must select at least one data entry point from each of the highlighted categories (although it is appreciated that some cases may require multiple selections within a category to fulfill the requirement and remove the highlight). For example, the user must indicate whether the broken humerus is open/closed, displaced/nondisplaced, etc. Therefore, deficient data entries may be gathered at or near the point of contact with the patient rather than based on additional or later knowledge.

Figure 21:
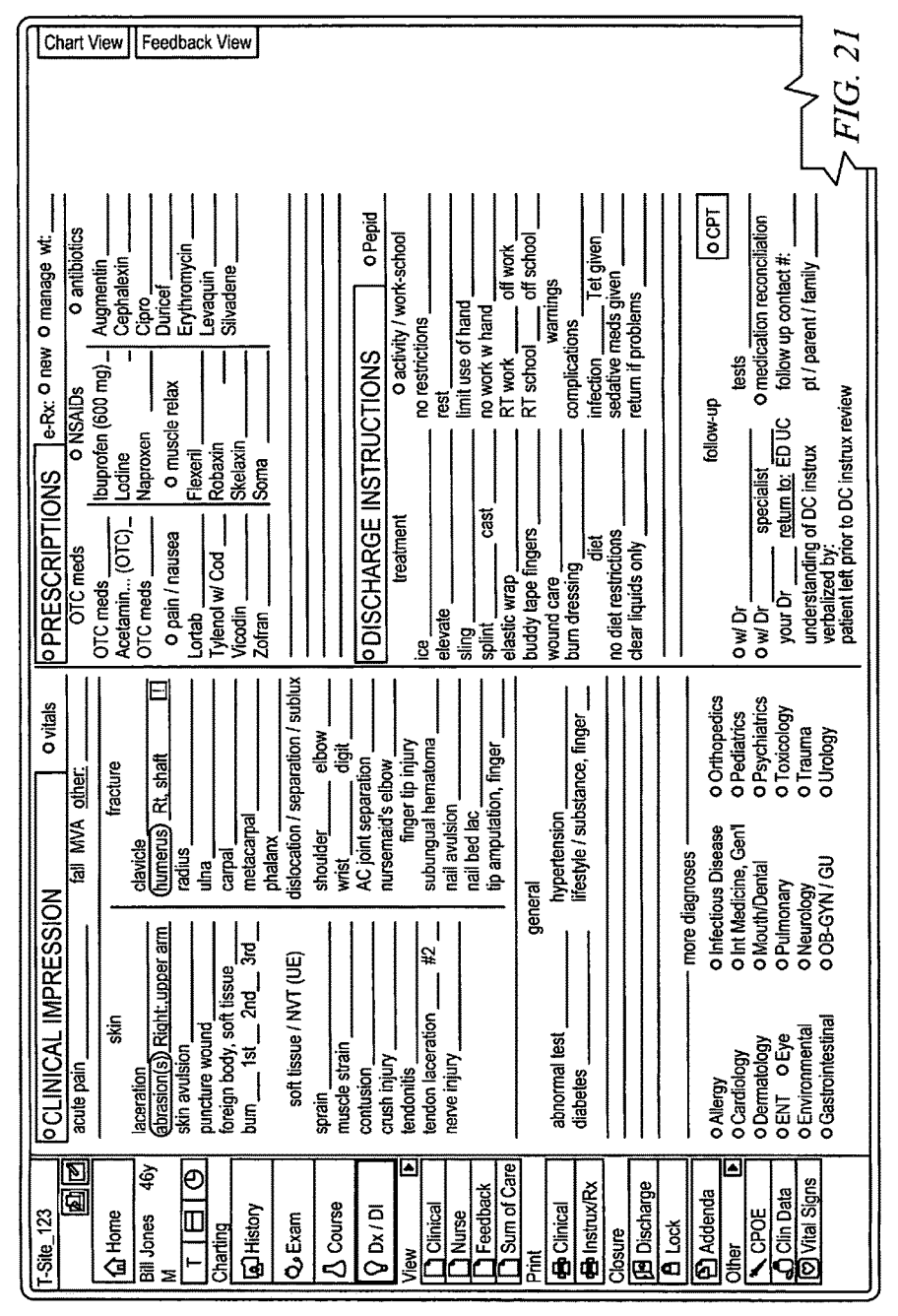

FIG. 21 illustrates an additional notification of deficiencies in entered data in accordance with another embodiment. After the humerus fracture content box has been closed, if there is no selection of data which has been indicated as missing, a notifier may be placed on the line item for the selected humerus fracture. This notifier may be implemented as an exclamation point as described with the previous example, whereupon a user may click or hover over the icon and see what information is missing. Further, clicking on the alert icon may link the user to a particular portion of the entry system where the missing information may be entered.

In the event that a user selects one or more items from within the highlighted categories of FIG. 20, the highlight of that category may disappear. For example, at FIG. 22 the user has selected the transverse data item, whereupon each of the other items in that category are no longer highlighted. The removal of the highlighting may indicate that a requirement for a specified diagnosis code has been satisfied. A user may continue to document/select items from within that group if appropriate. However, a disappearing highlight may symbolize that the present entry is sufficient for coding purposes.

Figure 23:
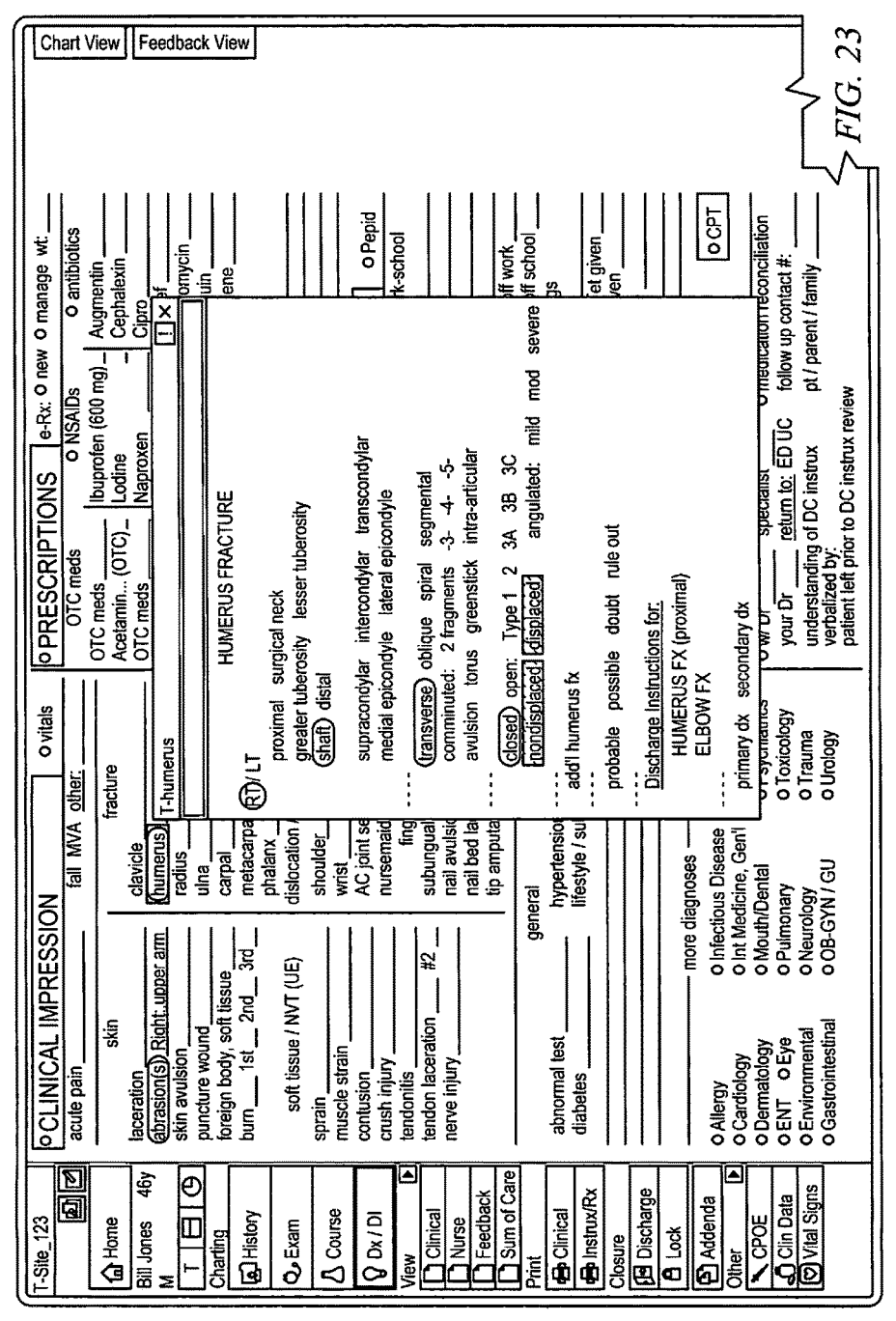
Figure 24:
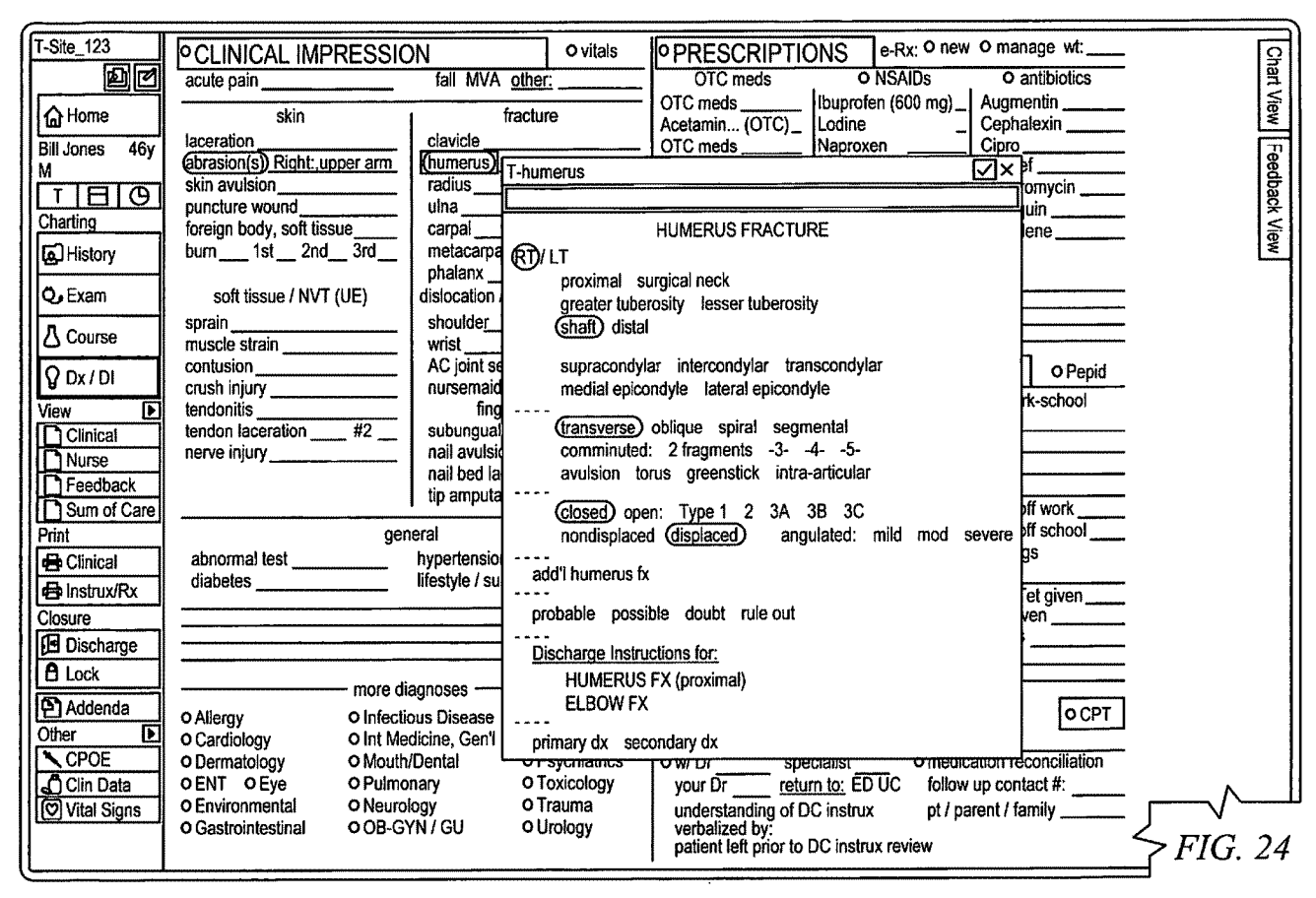

FIG. 23 illustrates additional categories being addressed by selecting the "closed" data point and FIG. 24 illustrates the final category being selected, whereupon all highlighted items have been addressed. In accordance with another embodiment, an indicator may be provided to the user to notify them that the appropriate data entry points have been received for generating a particular diagnosis code. This indicator may take any form. For example, in the illustrated embodiment the exclamation in the top right corner of the humerus fracture pop up window has been changed to a check mark icon to indicate that each requirement has been met.

It is noted that the illustrated embodiment is recognizing/correlating one diagnosis code with the data points being entered. In some instances multiple diagnoses may closely correlate with the received selections. In such circumstances, embodiments may add to the list of required items shown when hovering over the exclamation indicator. In some embodiments, multiple indicators may be given, each having their own listings of needed items that correspond to different diagnosis codes. Further, the marking or color coding of categories may include marking a first set of categories for a first diagnosis code and a second set for a second diagnosis code. Accordingly, the systems and methods described herein may be adapted to handle circumstances where multiple diagnoses exist and may function to notify a user when additional information is needed for the multiple diagnoses.

At FIG. 25, the physician may then complete the DX/DI template charting page for the patient encounter. This may include adding prescription information, discharge instructions, follow up recommendations, and the like.

Figure 27A:
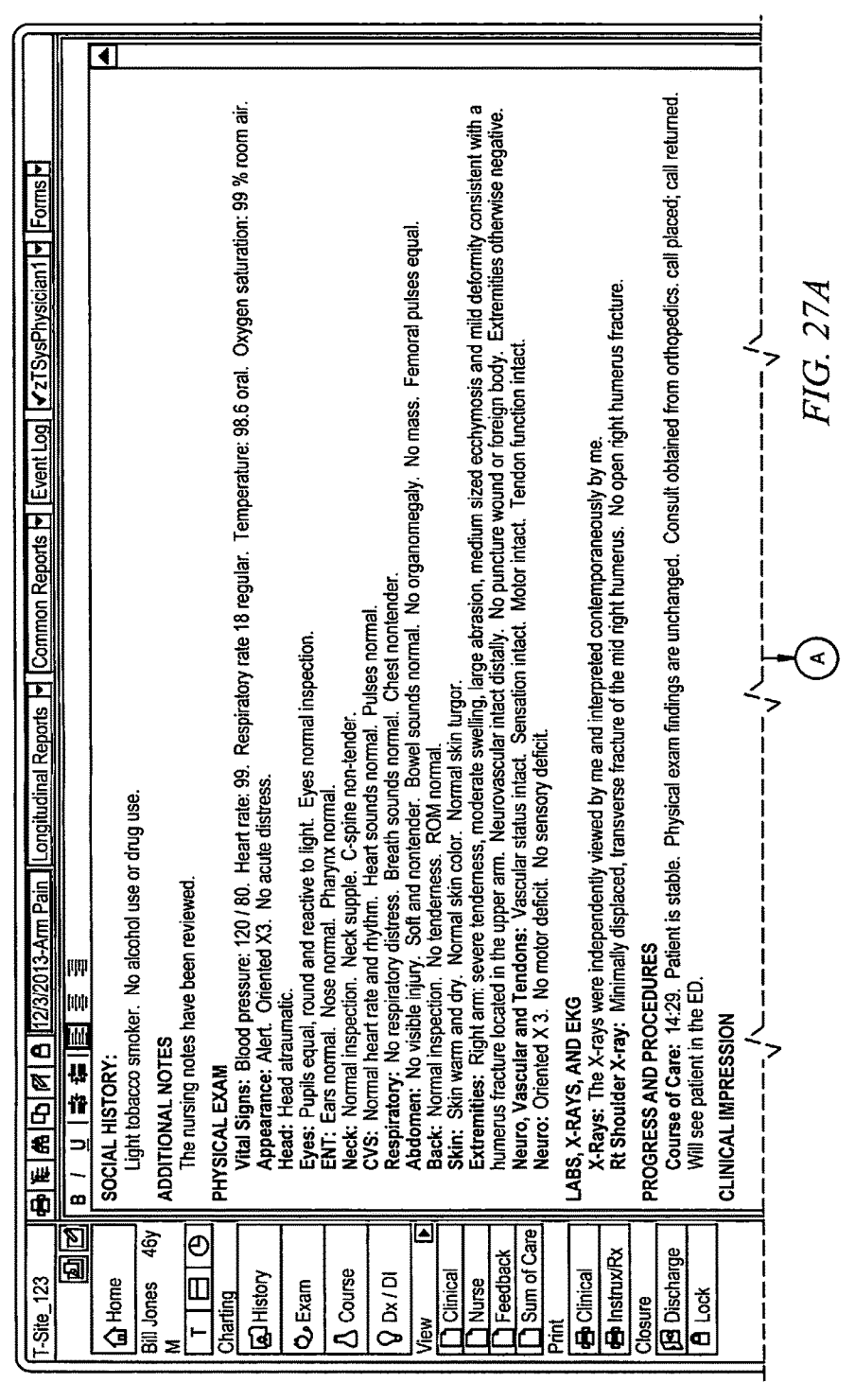

FIGS. 26 and 27 illustrate a medical report which is generated in response to the selected data elements which are selected throughout the course of the patient encounter. The line items of this report may be automatically generated and/or may be manually filled in by a medical professional. The information contained in the medical report may be further utilized by coding personnel to confirm or refine ICD-10 code selections. FIG. 28 illustrates instructions which may be given to a patient which contain pertinent information regarding the patient's diagnosis, recommendations/instructions for treatment and the like. Each of these reports may be automatically generated by the data entry system.

Figure 29:
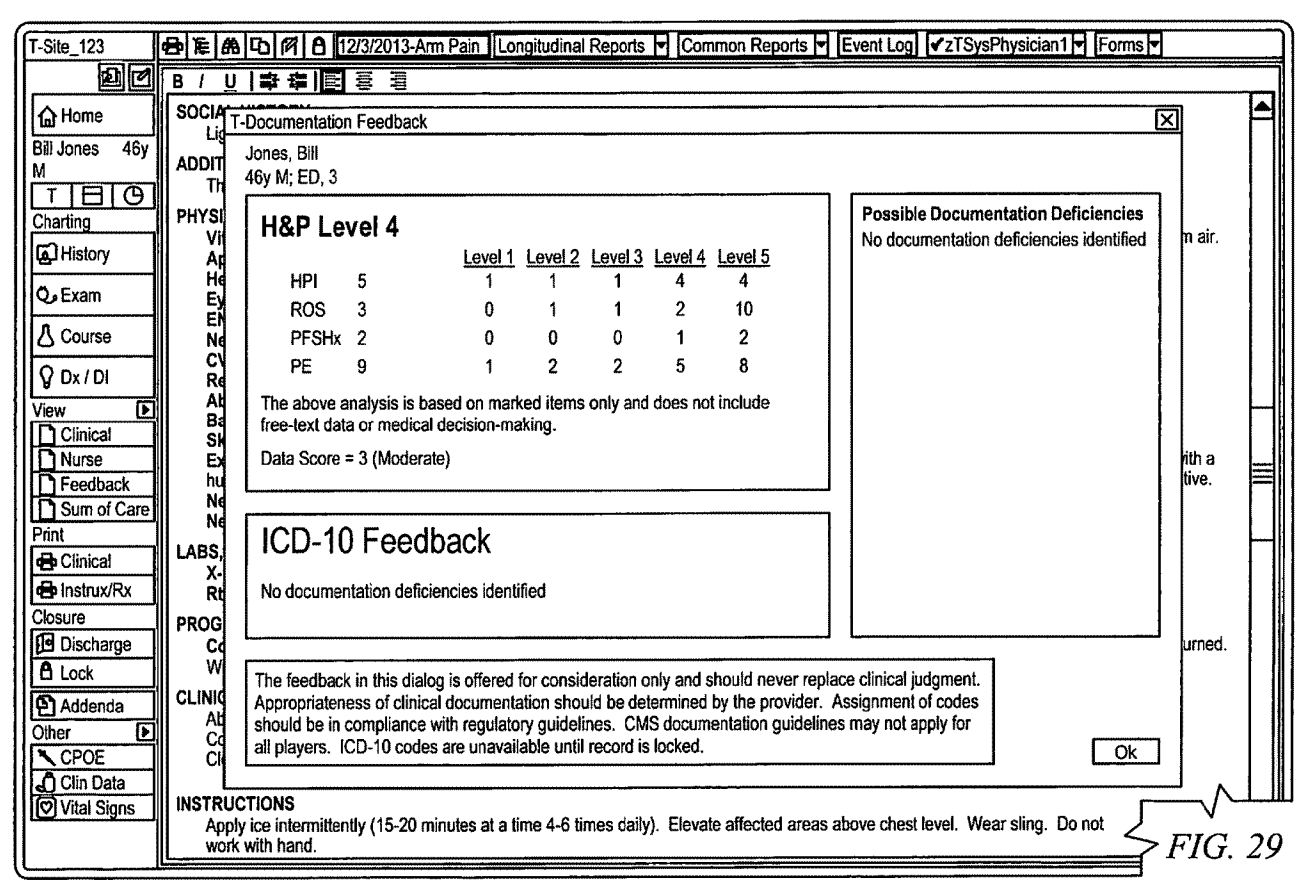

When the medical chart is ready to be finalized, embodiments may implement another error check procedure to insure that all necessary data has been obtained/documented. For example, if deficiencies relating to procedures, regulatory requirements and/or diagnosis coding information exists, a feedback report may be generated and provided to a user. Such feedback may be in the form of an error report or may be provided in any other manner to conveniently notify the user of missing information/data points. FIG. 29 illustrates such a report for the example patient. In this example, there are no ICD-10 deficiencies or any other deficiencies in documentation. In the event that an error exists, a link to the appropriate portion of the data entry system may be provided in the error report in order to allow a user quick access to remedy the errors.

A coding summary report may also be generated at FIG. 30. It is appreciated that data relevant to coding may be summarized and provided in the illustrated report in a manner that it may be utilized by another individual to generate the codes while having all necessary information for a particular code. Further, in some aspects the diagnosis codes may be automatically generated in response to the data item selections. Such diagnoses may be provided to the physician or another medical professional for approval or confirmation.

It is appreciated that the above workflow example may be altered in many ways while still remaining consistent with inventive concepts described herein. For example, portions of the charting process may be skipped all together. Further, information regarding coding may only be obtained, correlated, etc., at the stage of filling out the diagnosis template page. Additionally, it is noted that the particular layout of various screens is provided as an example that facilitates quick and easy selection of selectable data items for a user. Other layouts and/or displays may be utilized.

Figure 31:
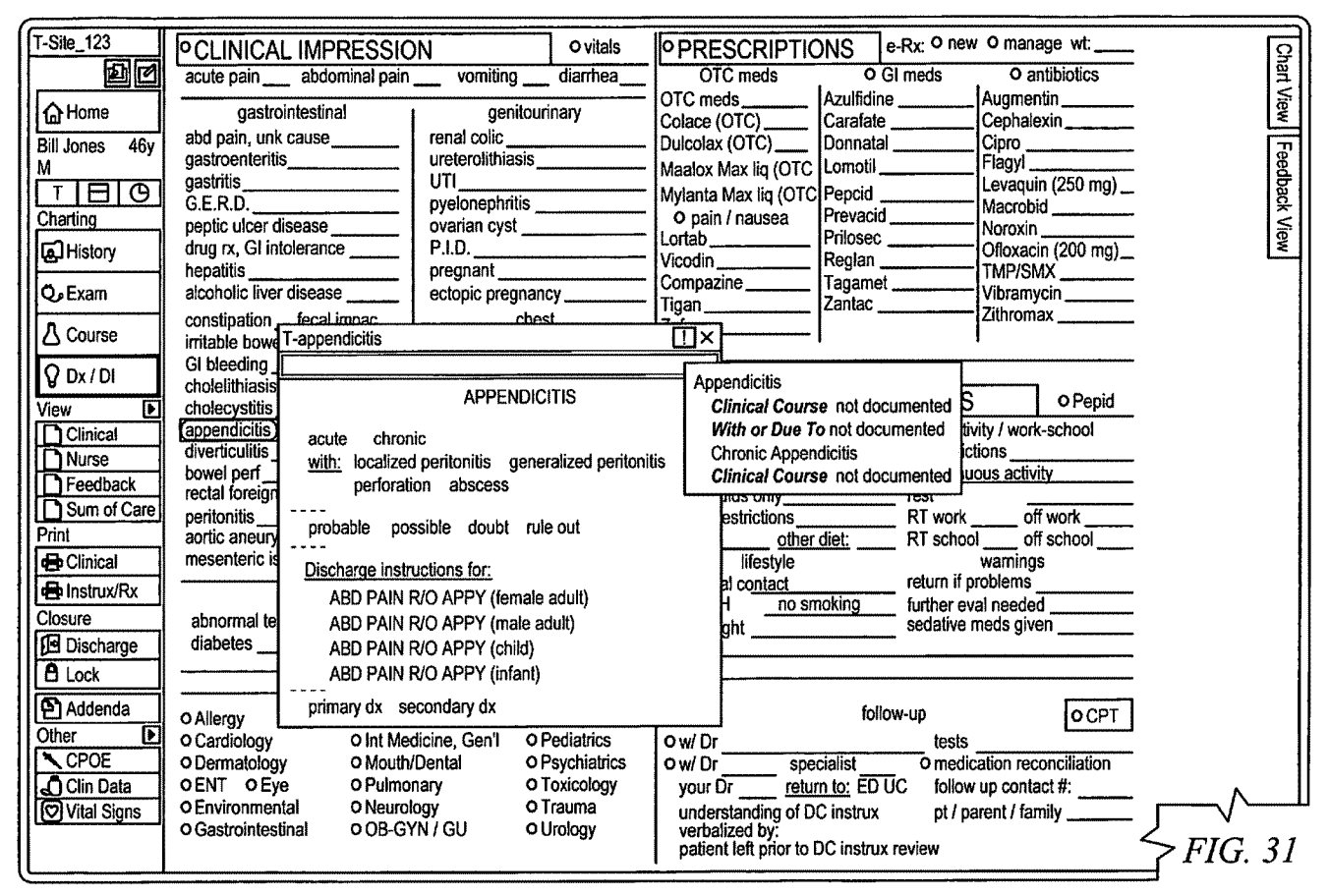

FIGS. 31-35 illustrate another example work flow in accordance with an embodiment of the present application. In this example, the chief medical complaint of "abdominal pain" from FIG. 2 has been selected. Referring to FIG. 31, in the DX/DI template screen the user has selected "appendicitis" which has caused a pop-up window to display. When clicking or hovering over the exclamation indicator in the pop-up window it can be seen that two different paths may be taken for providing the requisite information for different diagnosis codes. In one case, if the appendicitis is classified as "acute" additional information is needed, whereas if the appendicitis is classified as chronic, no other information is needed to correlate a particular diagnosis code.

Figure 32:
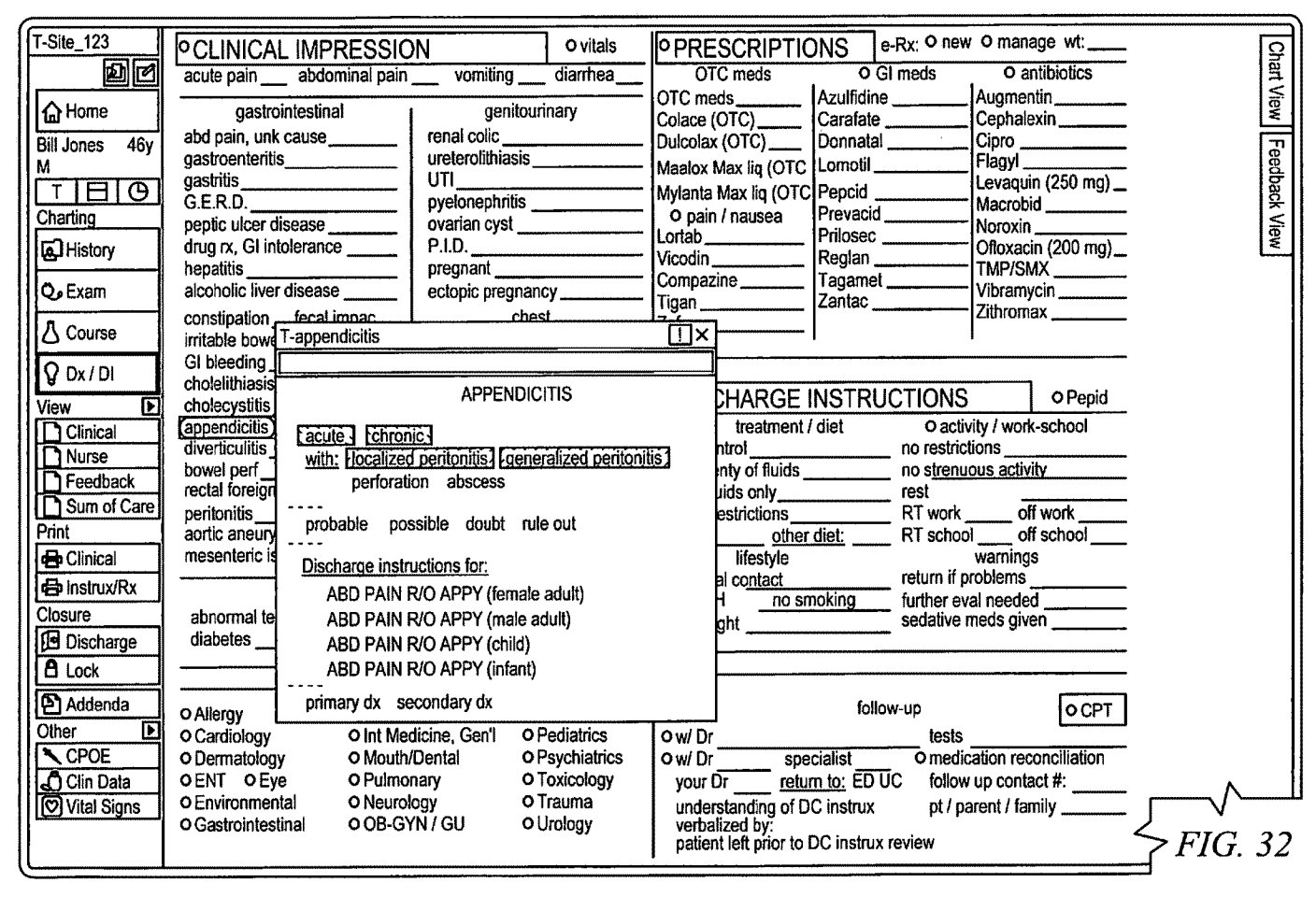
Figure 33:
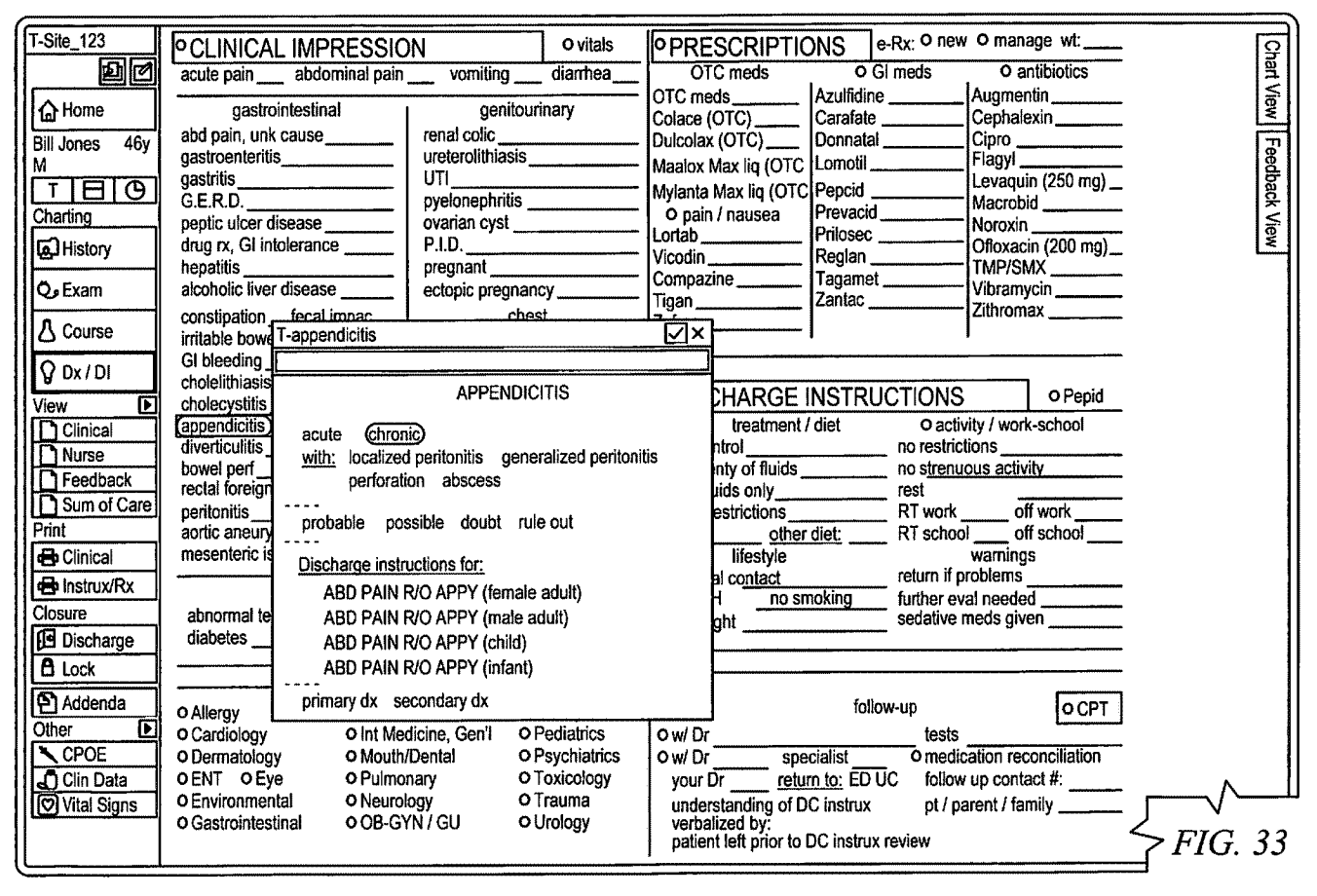
Figure 34:
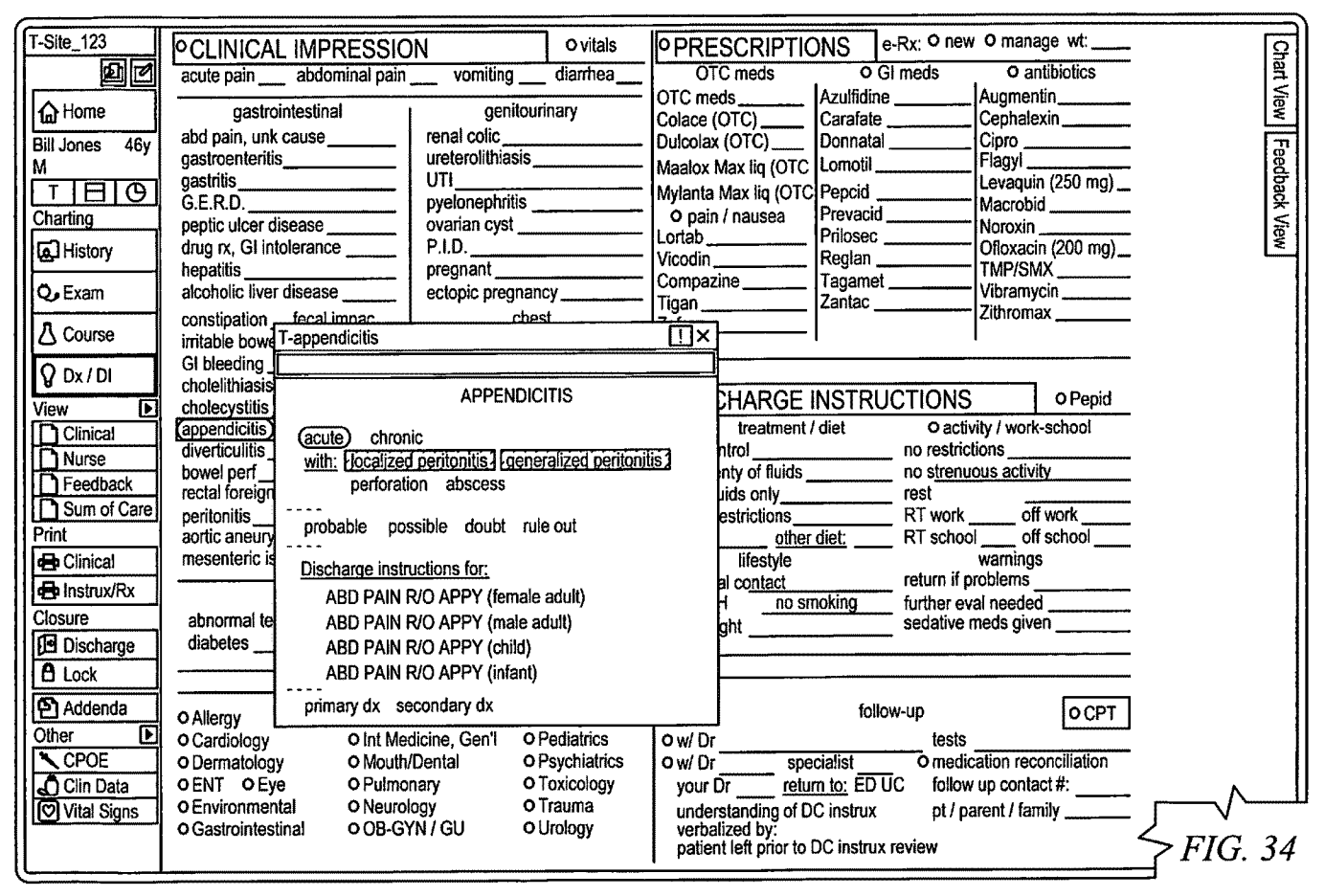
Figure 35:
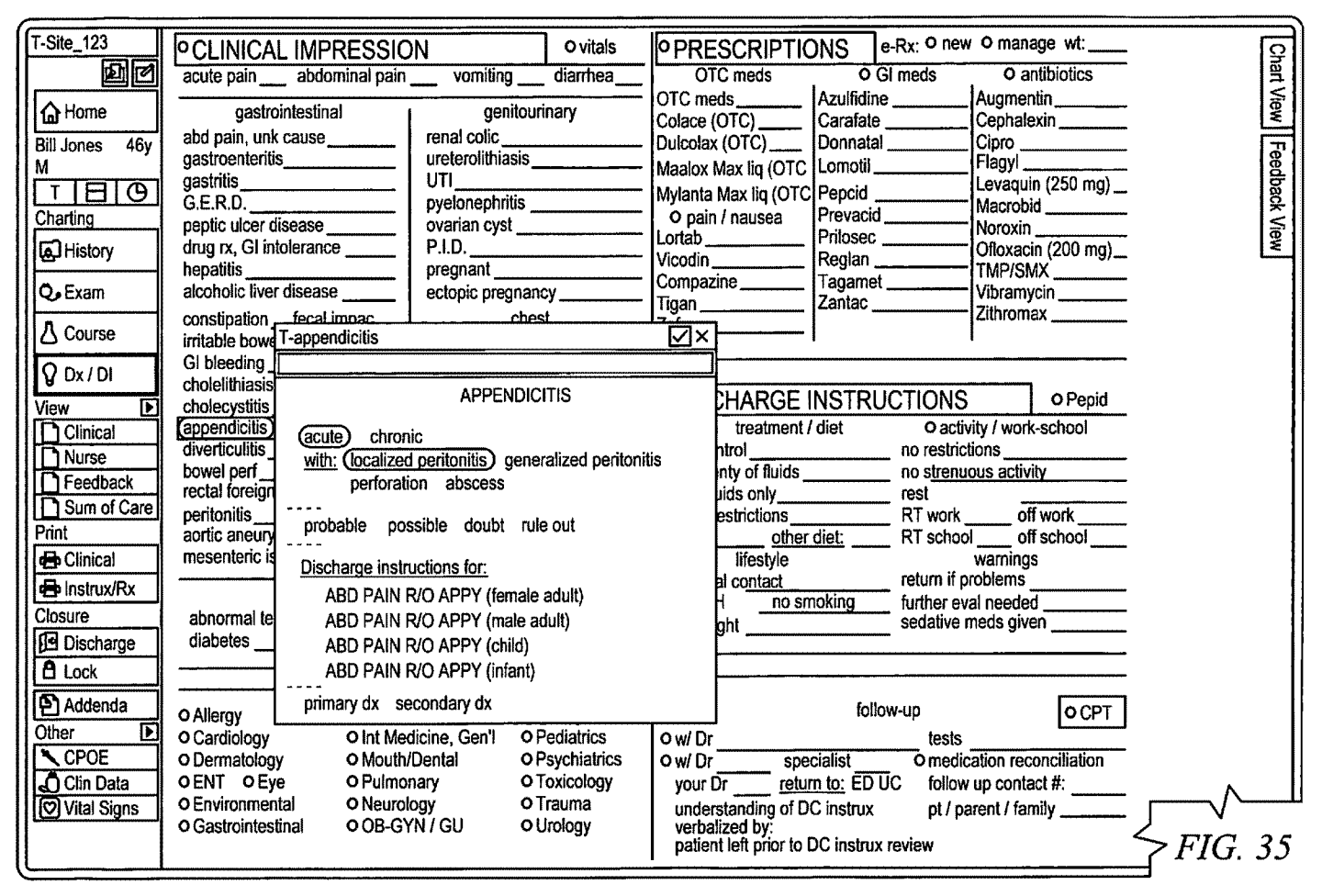

At FIG. 32, upon the user attempting to close a window, color coded required field selections become highlighted. It is appreciated that the second category is optional depending on the selection of acute or chronic appendicitis. In the event that "chronic" is selected (e.g. FIG. 33), the highlights on the second category may be removed and the exclamation indicator changes to a check mark to illustrate a positive correlation between entered data and a diagnosis code. Alternatively, as shown in FIG. 34, if "acute" is selected the second category of data remains highlighted and upon making a selection within the second category, highlights on the second category may be removed and the exclamation indicator changes to a check mark to illustrate a positive correlation between entered data and a diagnosis code as shown in FIG. 35.

In view of exemplary systems and functionality shown and described herein, methodologies that may be implemented in accordance with the disclosed subject matter will be better appreciated with reference to various functional block diagrams. While, for purposes of simplicity of explanation, methodologies are shown and described as a series of acts/blocks, it is to be understood and appreciated that the claimed subject matter is not limited by the number or order of blocks, as some blocks may occur in different orders and/or at substantially the same time with other blocks from what is depicted and described herein. Moreover, not all illustrated blocks may be required to implement methodologies described herein. It is to be appreciated that functionality associated with blocks may be implemented by software, hardware, a combination thereof or any other suitable means (e.g., device, system, process, or component). Additionally, it should be further appreciated that methodologies disclosed throughout this specification are capable of being stored on an article of manufacture to facilitate transporting and transferring such methodologies to various devices. Those skilled in the art will understand and appreciate that a methodology could alternatively be represented as a series of interrelated states or events, such as in a state diagram.

Figure 36:
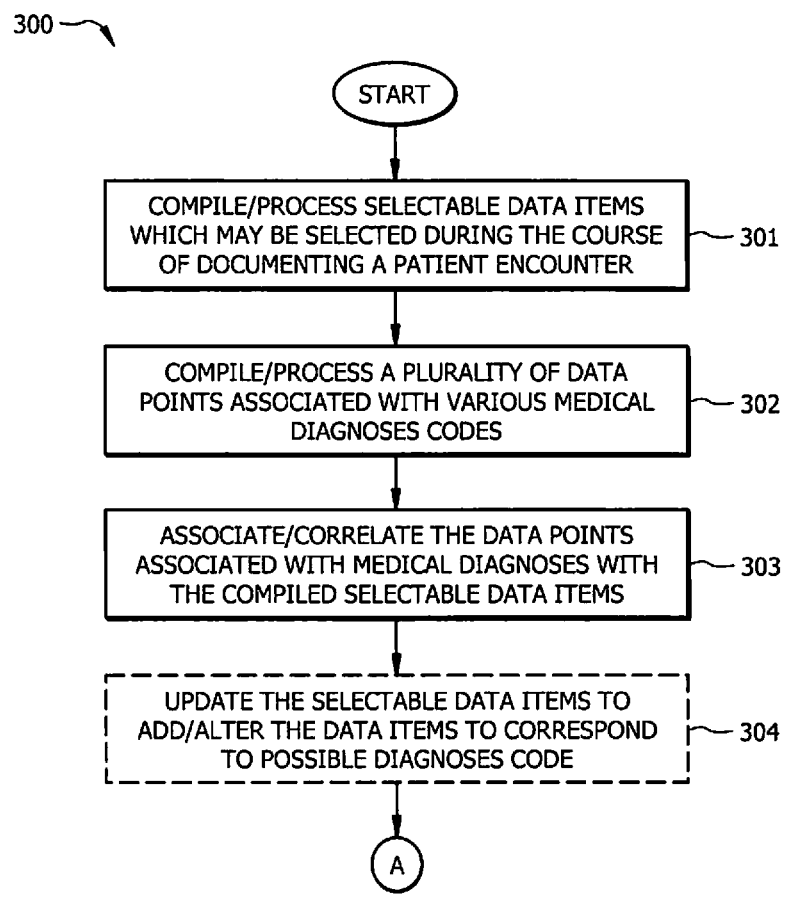
FIG. 36 illustrates a methodology operable on one or more processing devices for obtaining one or more diagnosis codes.

In accordance with one or more embodiments, with reference to FIG. 36, there is shown a methodology 300, operable on one or more processing devices for obtaining one or more diagnosis codes. Specifically, method 300 may involve, at 301 compiling or processing selectable data items which may be selected during the course of documenting a patient encounter. Such compiling may include determining what specific data items are present and determining what relations such data items have with each other. Method 300 may further include, at 302, compiling/processing a plurality of data points associated with medical diagnoses codes. For example, specific requirements for specific codes may be determined such as the requirement to specify which side of the body has a broken bone, etc.

At step 303, method 300 includes associating and/or correlating the data points associated with medical diagnosis and/or procedure codes of 302 with the compiled selectable data items of 301. Once the data points and delectable data items are associated with each other, systems may then monitor selected items and begin associating or predicting a possible code, and therefore prompt the user regarding whether additional data is needed, or if sufficient data has been received to generate a fully specified code.

Method 300 further includes optional step 304 which allows a system to update the selectable data items to add or alter these data items in order to closer correspond to a possible code. For example, if a diagnosis code requires a specific finding to be selected by a user, method 300 may add a selectable data element to the documentation system in order to allow for the selection of that finding.

Figure 37:
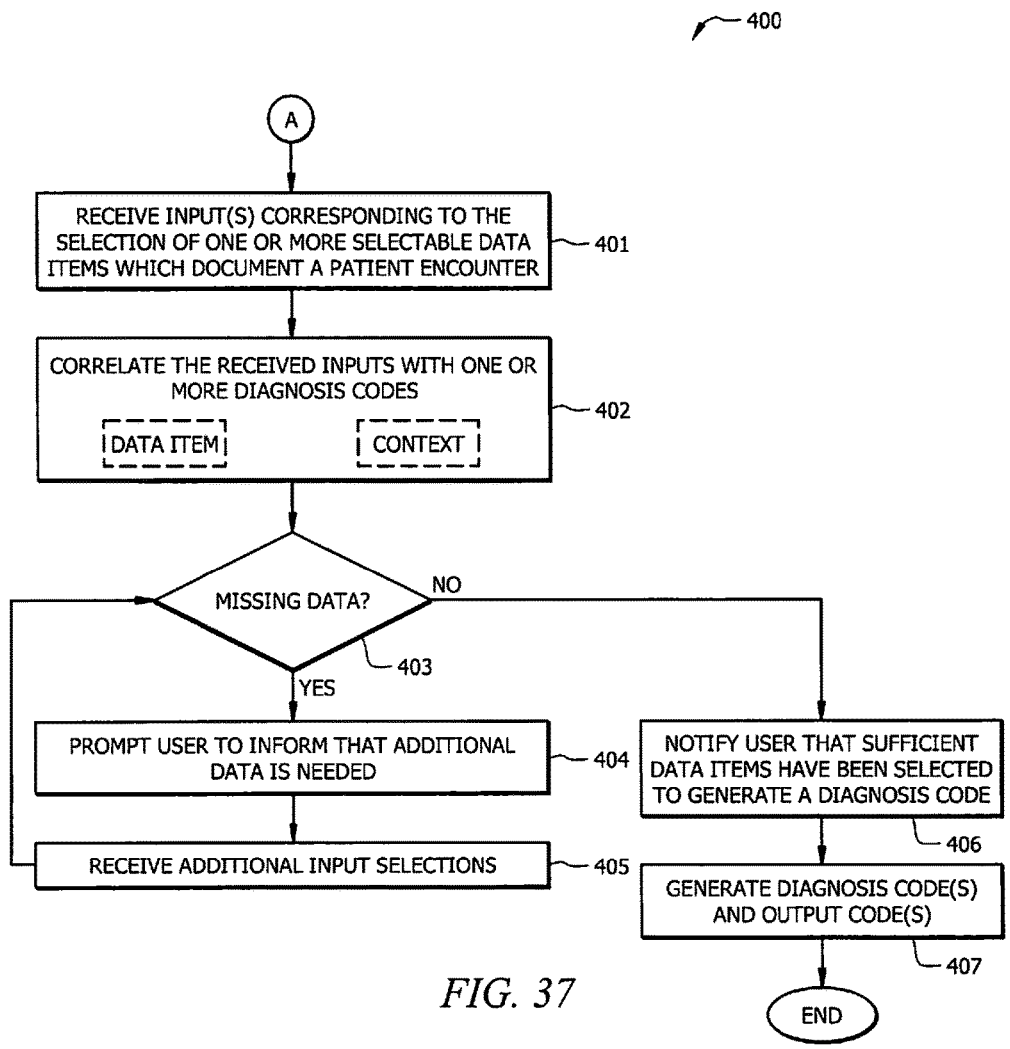
FIG. 37 illustrates a methodology operable on one or more processing devices for obtaining one or more diagnosis codes.

In accordance with one or more embodiments, with reference to FIG. 37, there is shown a methodology 400, operable on one or more processing devices for obtaining one or more diagnosis codes. It is noted that method 400 may be implemented as a continuation to method 300, or may be implemented separately. Method 400 may involve, at 401, receiving one or more inputs at a processing device that correspond to the selection of one or more selectable data elements which are selected to document a doctor-patient encounter. Such selections may be similar to those described above with respect to the charting application illustrated in FIGS. 1-35.

At step 402, method 400 includes correlating the received inputs with one or more diagnosis codes. It is appreciated that this correlation may include point to point correlation where selected data points align with required information for a diagnosis and/or procedure code. Alternatively or additionally, a contextual analysis of one or more inputs may be utilized to correlate the inputs to a code. For example, the finding of a diagnosis or procedure code may be seen as a dynamic calculation. Multiple selected items may include or exclude various diagnosis codes. For example, selecting a chief medical complaint of "abdominal pain" will likely rule out diagnoses that correspond to non-related issues such as a broken leg. Accordingly, a selection while not being directly on point with a diagnosis code, still provides contextual information. As a user selects additional items, target codes may be narrowed, changed, etc., which in turn may change the type of information that a user may be prompted to input in order to complete the information needed to generate a code.

At 403, method 400 determines whether there is missing data, e.g. whether the current selection of data items is insufficient to meet the elements of a fully specified diagnosis and/or procedure code. If there is missing data, at 404 a user may be prompted to provide additional data. This may be implemented in any manner which provides sufficient notification, e.g. as described above with respect to the exclamation point notification and/or color coded missing field indicators. Additional input selections may then be received at a processing device at step 405. Once there is no missing data (e.g. sufficient information exists to specify one or more diagnosis codes), a notification may be sent to the user that sufficient data items have been collected to generate a fully specified code at 406. Such a notification may be an affirmative notification or may be in the form of removing a notification that insufficient items have been selected.

In some embodiments, step 407 may be provided wherein a processing device may automatically generate one or more diagnosis codes and output these codes to a user or other processing device. Such a step is optional as the entered data may be sent to a coder who then manually selects and generates the codes.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A computer implemented method for controlling elements of a graphical user interface (GUI) for a medical data entry system, said method comprising:

configuring, at a processing device, a first GUI element to receive at least one input corresponding to at least one clinical concept associated with a diagnosis;

receiving, at said processing device, said at least one input corresponding to said at least one clinical concept associated with said diagnosis, wherein said at least one clinical concept is correlated with a plurality of diagnosis code values stored in a data base of said medical data entry system, wherein at least one diagnosis code value of said plurality of diagnosis code values is associated with a plurality of data requirements, wherein said at least one diagnosis code value is designated as a fully specified diagnosis code when said plurality of data requirements is met, wherein said plurality of data requirements includes one or more categories, having one or more selectable data items associated with each category of said one or more categories, said one or more selectable data items adapted to include a positive selection state and a negative selection state, and wherein said plurality of data requirements is considered met when at least one selectable data item from each of said one or more categories has been selected;

determining, in response to said receiving said at least one input, whether said plurality of data requirements associated with said at least one diagnosis code value has been met;

generating a second GUI element for presenting a textual representation of each of the one or more selectable data items;

activating a graphical indicator on the second GUI element, said graphical indicator indicating that said plurality of data requirements associated with said at least one diagnosis code value has not been met, and said graphical indicator indicating at least one category of the one or more categories for which an associated selectable data element has not been selected;

receiving a command to terminate said second GUI element; and in response to said receiving said command:
activating one or more graphical cues on said textual representation of said each of the one or more selectable data items based on said category of said each of the one or more selectable data items, wherein said one or more graphical cues correspond to different categories of said one or more categories;

applying a first control command to said GUI to prevent said second GUI element from terminating;

configuring said second GUI element to receive at least one selection representing the positive selection state, or the negative selection state of at least one of the one or more selectable data items associated with each respective category for which an associated selectable data element has not been selected;

determining whether a selection of at least one selectable data item from each of said one or more categories has been received by said GUI;

in response to determining that a selection of at least one selectable data item from each of said one or more categories has been received by said GUI:

designating said at least one diagnosis code value as a fully specified diagnosis code;

modifying said graphical indicator to indicate that said plurality of data requirements associated with said at least one diagnosis code value has been met; and applying a second control command to said GUI to enable termination of said second GUI element.

2. The method of claim 1, wherein determining that said plurality of data requirements associated with said at least one diagnosis code value has been met comprises providing said fully specified diagnosis code to said user.

3. The method of claim 2 wherein said activating said one or more graphical cues on said textual representation of said each of the one or more selectable data items includes utilizing color to identify selectable data elements of a second category which represents that an item in said first category must be positively or negatively selected, wherein said utilizing color to identify selectable data elements of said first category is implemented with a different appearance than the color utilized to identify selectable data elements of said second category.

4. The method of claim 1, further comprising notifying a user when said plurality of data requirements associated with said at least one diagnosis code value has been met by said positive or negative selection of said selectable data elements from each of said one or more categories, wherein said notifying said user when said plurality of data requirements associated with said at least one diagnosis code value has been met comprises providing said fully specified diagnosis code to said user.

5. The method of claim 1 wherein said selection of at least one selectable data element is based on selectable information gathered during one or more phases of a patient encounter.

6. The method of claim 5 wherein said one or more phases include one or more of a history portion, physical examination portion, and a course portion.

7. A computer-based tool for controlling elements of a graphical user interface (GUI) for a medical data entry system, comprising:

a non-transitory computer-readable medium comprising code for causing one or more devices to:

configure a first GUI element to receive at least one input corresponding to at least one clinical concept associated with a diagnosis;

receive said at least one input corresponding to said at least one clinical concept associated with said diagnosis, wherein said at least one clinical concept is correlated with a plurality of diagnosis code values stored in a data base of said medical data entry system, wherein least one diagnosis code value of said plurality of diagnosis values is associated with a plurality of data requirements, wherein said at least one diagnosis code value is designated as a fully specified diagnosis code when said plurality of data requirements is met, wherein said plurality of data requirements includes one or more categories having one or more selectable data items associated with each category of said one or more categories, said one or more selectable data items adapted to include a positive selection state and a negative selection state, and wherein said plurality of data requirements is considered met when at least one selectable data item from each of said one or more categories has been selected;

determine, in response to receiving said at least one input, whether said plurality of data requirements associated with said at least one diagnosis code value has been met;

generate a second GUI element for presenting a textual representation of each of the one or more selectable data items;

activate a graphical indicator on the second GUI element, said graphical indicator indicating that said plurality of data requirements associated with said at least one diagnosis code value has not been met, and said graphical indicator indicating at least one category of the one or more categories for which an associated selectable data element has not been selected;

receive a command to terminate said second GUI element; and in response to said receive said command:

activate one or more graphical cues on said textual representation of said each of the one or more selectable data items based on said category of said each of the one or more selectable data items, wherein said one or more graphical cues correspond to different categories of said one or more categories;

apply a first control command to said GUI to prevent said second GUI element from terminating;

configure said second GUI element to receive at least one selection representing the positive selection state, or the negative selection state of at least one of the one or more selectable data items associated with each respective category for which an associated selectable data element has not been selected;

determine whether a selection of at least one selectable data item from each of said one or more categories has been received by said GUI; and in response to determine that a selection of at least one selectable data item from each of said one or more categories has been received by said GUI:

designate said at least one diagnosis code value as a fully specified diagnosis code;

modify said graphical indicator to indicate that said plurality of data requirements associated with said at least one diagnosis code value has been met; and apply a second control command to said GUI to enable termination of said second GUI element.

8. The computer-based tool of claim 7 wherein said graphical indicator lists said at least one category of the one or more categories for which an associated selectable data element has not been selected.

9. The computer-based tool of claim 7 wherein activating said one or more graphical cues on said textual representation of said each of the one or more selectable data items includes code for causing one or more devices to utilize color to identify selectable data elements of a first category which represents that an item in said first category must be positively or negatively selected.

10. The computer-based tool of claim 9 wherein said activating said one or more graphical cues on said textual representation of said each of the one or more selectable data items includes code for causing one or more devices to utilize color to identify selectable data elements of a second category which represents that an item in said first category must be positively or negatively selected, wherein said code for causing the one or more devices to utilize color to identify said selectable data elements of said first category is implemented with a different appearance than the color utilized to identify said selectable data elements of said second category.

11. The computer-based tool of claim 7, further code for causing the one or more devices to notify a user when said plurality of data requirements associated with said at least one diagnosis code value has been met by said positive or negative selection of said selectable data elements from each of said one or more categories, wherein said code for causing the one or more devices to notify said user when said plurality of data requirements associated with said at least one diagnosis code value has been met comprises code for causing one or more devices to provide said fully specified diagnosis code to said user.

12. The computer-based tool of claim 7 wherein said selection of at least one selectable data element is based on selectable information gathered during one or more phases of a patient encounter.

13. The computer-based tool of claim 12 wherein said one or more phases include one or more of a history portion, physical examination portion, and a course portion.

* * * * *